(12) United States Patent
Rubio et al.

(10) Patent No.: US 9,814,242 B2
(45) Date of Patent: *Nov. 14, 2017

(54) BACILLUS SUBTILIS ISOLATE FROM CORN AND EXTRACTS THAT INHIBIT THE GROWTH OF UNDESIRABLE MICROORGANISMS IN FOOD PRODUCTS

(71) Applicant: INVESTIGACIÓN TECNICA AVANZADA, S.A. DE C.V., Guadalupe (MX)

(72) Inventors: Felipe A. Rubio, Edinburg, TX (US); Roberto Contreras, Guadalupe (MX); J. Fernando Ramirez, Guadalupe (MX)

(73) Assignee: GRUMA S.A.B. DE C.V., San Pedro Garza Garcia (MX)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,541

(22) Filed: Sep. 22, 2015

(65) Prior Publication Data

US 2016/0007614 A1  Jan. 14, 2016

Related U.S. Application Data

(63) Continuation-in-part of application No. 13/823,530, filed as application No. PCT/US2011/051575 on Sep. 14, 2011, now Pat. No. 9,144,588.

(60) Provisional application No. 61/383,169, filed on Sep. 15, 2010.

(51) Int. Cl.
| | |
|---|---|
| *A01N 63/02* | (2006.01) |
| *A21D 2/08* | (2006.01) |
| *A23L 3/3463* | (2006.01) |
| *A23L 3/3571* | (2006.01) |
| *A21D 2/26* | (2006.01) |
| *A21D 15/00* | (2006.01) |
| *A23B 9/28* | (2006.01) |

(52) U.S. Cl.
CPC .......... *A01N 63/02* (2013.01); *A21D 2/267* (2013.01); *A21D 15/00* (2013.01); *A23B 9/28* (2013.01); *A23L 3/34635* (2013.01); *A23L 3/3571* (2013.01)

(58) Field of Classification Search
None
See application file for complete search history.

(56) References Cited

U.S. PATENT DOCUMENTS

| | | |
|---|---|---|
| 5,919,695 A | 7/1999 | Vedamuthu et al. |
| 6,183,736 B1 | 2/2001 | Moyne et al. |
| 6,355,289 B1 | 3/2002 | Rolow et al. |
| 2005/0271643 A1 | 12/2005 | Sorokulova et al. |

OTHER PUBLICATIONS

Derrien et al., "Fate, Activity, and Impact of Ingested Bacteria Within the Human Gut Microbiota", Trends in Microbiology, Jun. 2015, vol. 23, No. 6.
Rose et al., "Methods for Reducing Microbial Contamination of Wheat Flour and Effects on Functionality", Cereal Foods World, May-Jun. 2012, vol. 57, No. 3.
Bourdichon et al, "Food Fermentations: Microorganisms With Technological Beneficial Use", International Journal of Food Microbiology, 154 (2012) 87-97.
Adolphson et al., "Isolation and Characterization of the Microflora of Nixtamalized Corn Masa", International Journal of Food Microbiology 165 (2013) 209-213.
Jenson et al. "The Use of Nisin As a Preservative in Crumpets" Journal of Food Protection, vol. 57 (1994) pp. 874-877.
Bothast et al., Microbiology of Corn and Dry Milled Corn Products, Presented at the Institute of Food Technologists' Meeting, Miami Beach, Jun. 10-14, 1973.
Dietert et al., "The Microbiome and Sustainable Healthcare", Healthcare 2015, 3, pp. 100-129; doi:10.3390/healthcare3010100, ISSN 2227-9032.
De Vuyst et al., "Microbial Ecology of Sourdough Fermentations: Diverse or Uniform?", Food Microbiology 37 (2014) 11-29.
Sperber, "Role of Microbiological Guidelines in the Production and Commercial Use of Milled Cereal Grains: a Practical Approach for the 21st Century", Journal of Food Protection. vol. 70, No. 4, 2007, pp. 1041-1053.
Brandt, "Starter Cultures for Cereal Based Foods", Food Microbiology 37 (2014) 41-43.
Vojnovich et al., "Reducing Microbial Populations in Dry-Milled Corn Products", Cereal Science Today (1970).
Rao, "Aseptic Processing of Foods", 8 (1990).
International Search Report for PCT/US2011/051575 dated Oct. 20, 2011.
K.E. Sutyak et al: "Isolation of the Bacillus subtilis antimicrobial peptide subtilosin from the dairy product-derived Bacillus amyloliquefaciens", Journal of Appli Ed Microbiology, vol. 104, No. 4, Apr. 1, 2008 (Apr. 1, 2008), pp. 1067-1074, XP55009965, ISSN: 1364-5072, D01: 10.IIII/j.1365-2672.2007.03626.x, p. 1067-p. 1074.
Pinchuk I V et al: "In vitro anti-Helicobacter pylon activity of the probiotic strain Bacillus subtilis 3 is due to secretion of antibiotics", Antimicrobial Agents and Chemotherapy, American Society for Microbiology, DC, US, vol. 45, No. 11, Nov. 1, 2001 (Nov. 1, 2001), pp. 3156-3161, XP002375506, ISSN: Washington, 0066-4804, D01: 10.1128/AAC.45.11.3156-3161.2001, p. 3156-p. 3161.

(Continued)

*Primary Examiner* — Michelle F Paguio Frising
(74) *Attorney, Agent, or Firm* — Young & Thompson

(57) ABSTRACT

Biologically pure cultures of *Bacillus subtilis* Maseca-1 strain were isolated from the pericarp of nixtamalized corn. The *Bacillus* Maseca-1 strain was characterized and found to produce peptides and/or other compounds that have antimicrobial activity. An extract prepared from the *Bacillus* Maseca-1 strain is active against microorganisms such as bacteria and mold and may be used as an agent to inhibit the growth of undesirable microorganisms and thereby prevent spoilage and extend the shelf life in foods.

8 Claims, 15 Drawing Sheets

(56) References Cited

OTHER PUBLICATIONS

Maget-Dana, R., and Peypoux, F. "Iturins, a special class of pore-forming lipopeptides: biological and physicochemical properties", vol. 1994, pp. 151-174.

Genomic DNA fingerprint

BACILLUS SUBTILIS ISOLATE FROM CORN AND EXTRACTS THAT INHIBIT THE GROWTH OF UNDESIRABLE MICROORGANISMS IN FOOD PRODUCTS

FIELD OF THE INVENTION

The present invention relates to isolated biologically pure cultures of a novel spore forming *Bacillus* species, and more particularly, to a *Bacillus subtilis* Maseca-1 isolate. The invention also relates to extracts prepared from the Maseca-1 strain that can inhibit the growth of undesired microorganisms in food and food products, and thereby reduce spoilage and increase shelf-life.

BACKGROUND OF THE INVENTION

Research on antimicrobial peptides has been pursued for more than four decades. This field has attracted a great deal of attention, searching among microbial species from virtually any corner of the planet, to find microbes as a potential source of therapeutic agents that can be screened for antimicrobial, antifungal, antiviral, immunomodulating, immunosuppressive, anti-inflammatory and antitumor activities. These small peptides or lantibiotics (<4 kDa) are characterized by their high content of thioether linked amino acid residues and unsaturated dehydrated residues.

The lantibiotics are very active against pathogenic Gram positive bacteria (e.g., *B. cereus*) and fungi (e.g., *A. flavus*) that are directly responsible for some food borne illnesses. This class of peptides has the capacity to be used as a biopreservative to protect perishable food products from pathogen contamination, prevent spoilage, inhibit pathogens and prevent infections in humans and animals.

Various microbial species have also been shown to produce a variety of secondary metabolites of interest and utility. Among these are small peptide molecules that represent a very large and diverse subclass of bioactive natural products that have unique structural features involved in the morphology, physiology and survival of the microbe. There are, for example, amphiphilic lipopeptides which are aggressive surface tension reducing agents, such as surfactin and the antifungal mycosubtilin. In these compounds, the lipo-substituent plays a key role in disrupting the cell membrane, while the amphiphilic component exhibits disruptive hemolytic properties. These properties make them very strong antiviral and antibacterial compounds.

Consumption of certain live microorganisms has been shown in some circumstances to have a beneficial impact on man and animals. A diverse group of microbes has been evaluated for such "probiotic" activity, including many species of the genera Lactobacilli and Bifidobacteria. They are the most abundant in probiotic-containing food products. Less commonly, species of *Enterococcus, Saccharomyces*, non-pathogenic *Escherichia*, and spore-forming *Sporolactobacillus, Brevibacillus* and non-pathogenic *Bacillus*, have been suggested for probiotic foods.

The commensal microflora in the intestine is a complex ecosystem with interactions among host cells, nutrients and microflora. An adult human body contains a living bacterial biomass of greater than $10^{14}$ and more than 400 different species. The probiotic bacteria help to keep pathogenic bacteria at bay. Also, "symbiotic" bacteria from industrial and traditional fermented foods may also contribute to the development of a healthy gastrointestinal microflora (e.g., a significant enrichment in the bacterial phylum Bacteriodetes and depletion in the bacterial phylum Firmicutes in the human gut microbiota).

The "hygiene hypothesis" proposed in 1989 by David Strachan correlated lower environmental exposure to microbes—as seen in developed countries—with higher rates of allergies. Western developed countries successfully controlled infectious diseases during the second half of the 20th century by improving sanitation and by using antibiotics and vaccines. At the same time, a rise in new diseases occurred such as allergies, autoimmune disorders, and inflammatory bowel disease (IBS) both in adults and in children. The gastrointestinal microflora are known to play an important role in IBS pathogenesis. Obesity is also associated with an imbalance in the normal gut microbiota.

Corn tortillas are a common staple in the diets of the Mexican, Mexican-American and Central American populations. Traditionally, corn tortillas are prepared by steeping whole-kernel corn overnight in a lime solution (1 to 2% w/w), and subsequently grinding the drained and rinsed and/or peeled grain (now referred to as nixtamal) into a fresh dough called masa (56% moisture content). Natural fermentation and souring in the masa can lead to microbial spoilage, often within 5-12 hours. Commercially, the dough is stacked at ambient temperature and held for a period of time (a few minutes to several hours) before being formed and baked into tortillas (45-50% final moisture).

Commercial tortilla mills (Central Mexico) have been shown to produce corn dough with counts of lactic acid bacteria (i.e., *Streptococcus* spp. and *Lactobacillus* spp.) and aerobic mesophiles (i.e., *Streptococcus bovis*) ranging from 10,000 to 10,000,000 CFU/g. Coliforms were also found from 100 to1000 CFU/g, while fungal counts were <10 CFU/g (Adolphson et al., 2013).

Studies of fermented maize foods in southeastern Mexico found lactic acid bacteria (i.e., *Leuconostoc* and *Lactococcus* spp.) present at 100,000-1,000,000 CFU/g in pozol, a fermented nixtamalized corn dough consumed as a beverage mainly by the indigenous Mayan populations (Wacher et al., 2000). A mixed-culture fermentation was typical in pozol and a varied microflora have been isolated (Ulloa et al., 1983; Ramirez, 1987; and Steinkraus, 1996) such as spore forming bacteria (*B. cereus* and *Bacillus* spp.), coliform bacteria (*E. coli* and *K. pneumonia*), free-living nitrogen fixing bacteria (*K. pneumonia* and *A. pozolis*), lactic acid bacteria (*Lactobacillus* spp.) and yeast and molds (*Candida* spp., *Geotrichum candidum, Monilia sitophila* and *Penicillium* sp.).

The ecology of food fermentation and spoilage includes several factors: (a) intrinsic factors (physico-chemical properties of the food material), (b) microbiological changes due to the modes of processing (endogenous or exogenous microorganisms), (c) extrinsic factors (water activity, oxygen tension and temperature) and (d) implicit factors (symbiosis or antagonism amongst microflora). The North American Millers Association (NAMA) published a survey for the microbiological profile of five dry-milled grains (wheat, corn, oats, whole wheat and durum) showing similar or reduced counts for indicator tests (total aerobes, fungi, coliform and *E. coli*) (Sperber et al., 2007.

Food processing technologies allow many products to be marketed safely, and the keeping quality depends on the formulation of chemical (inorganic/organic acids) and novel compounds that inhibit microbial growth and control the microbial ecology in the food production environment. Natural and/or biocidal agents include antimicrobial compounds from plants, bacteria and animals, and cultures (e.g. probiotics excreting bacteriocins and lantibiotics).

SUMMARY OF THE INVENTION

The present invention relates to isolated biologically pure cultures of a novel spore forming *Bacillus* species, and more particularly, to *Bacillus subtilis* Maseca-1, ATCC Accession Number PTA-8831. The present invention also relates to peptides produced by Maseca-1 having antimicrobial activity. The present invention further relates to probiotic compositions that contain Maseca-1.

The present invention includes methods of preventing or inhibiting the growth of a wide variety of undesirable microorganisms, such as bacteria, mold and sporeforming microflora, utilizing an extract produced by the Maseca-1. In particular, the Maseca-1 extract can inhibit the growth of microorganisms in foods and food products, such as in flour and flour-based foods. The extract can inhibit the growth of microorganisms in raw dough as well as in cooked products such as tortillas. Inhibiting the growth of microorganisms provides for extended storage times of the foods and food products through reduced fermentation and spoilage.

The present invention includes methods for extending the shelf life of food products, in particular flour based products such as tortilla, by adding to the food product an effective amount of a Maseca-1 extract.

BRIEF DESCRIPTION OF THE DRAWINGS

FIG. 8A for bacteria count and FIG. 8B for mold count.

FIG. 8C shows bacterial counts from freshly prepared tortilla and FIG. 8D shows bacterial counts after 3 days storage at 25° C.

DETAILED DESCRIPTION OF THE INVENTION

Figure 1:
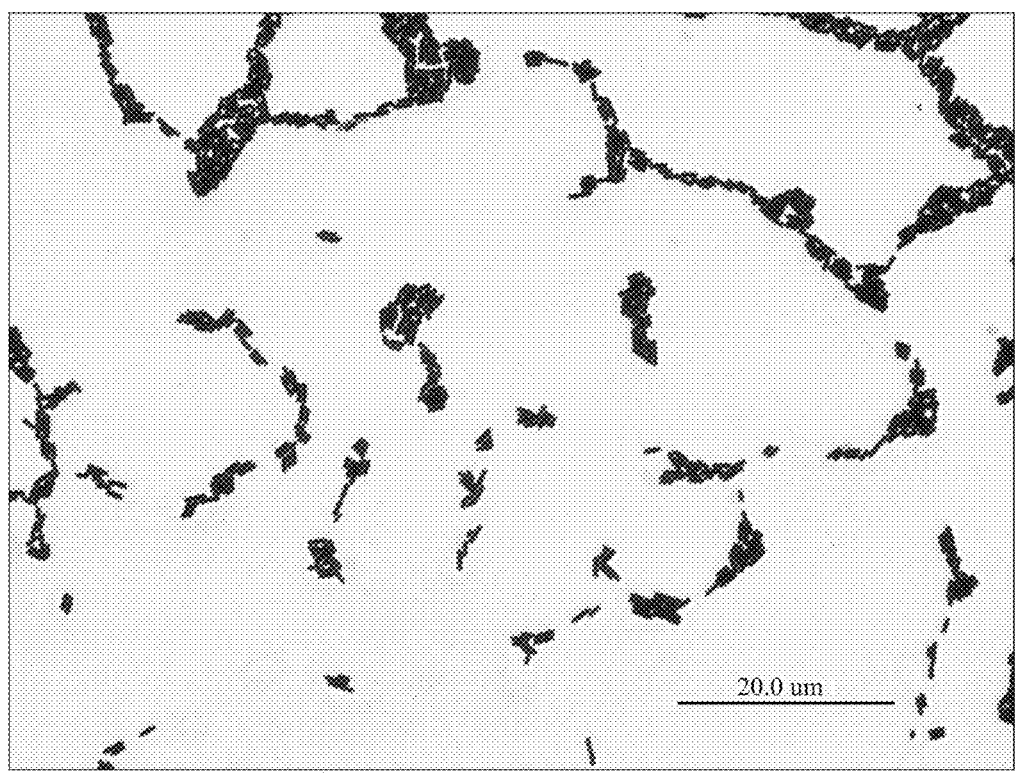
FIG. 1 illustrates a light microscopy image of the *Bacillus subtilis* Maseca-1 vegetative cells.

The present invention relates to an isolated biologically pure culture of a novel spore forming *Bacillus* species, and more particularly, to *Bacillus subtilis* Maseca-1 isolated from the pericarp of nixtamalized whole corn. The *Bacillus subtilis* Maseca-1 strain has been deposited as ATCC Accession Number PTA-8831.

The present invention also relates to a method for inhibiting undesirable microorganisms in food, food products, and food materials such as nixtamalized corn flour, dough and tortilla by exposing the food material to an effective amount of inhibitor of the undesired microorganisms extracted from a culture of the *Bacillus subtilis* Maseca-1 deposited as ATCC Accession Number PTA-8831. The present invention can prevent or reduce the amount of spoilage in the food, food products and food material, and thereby extend the shelf life of such products.

An extract prepared from the Maseca-1 can be added to the food, food product or food material to inhibit the growth of undesirable microorganisms, such as mold and bacteria, reducing or preventing spoilage, and thereby extending the shelf life. The Maseca-1 extract can be added at any stage of food preparation. For example, the Maseca-1 extract can be added to raw or uncooked dough and the dough will benefit from the inhibited growth, reduced spoilage and extended shelf life. The Maseca-1 extract can also be added to the raw dough and the food product prepared from the dough, such as cooked tortilla, will benefit from the inhibited growth, reduced spoilage and extended shelf life.

The following description, taken in conjunction with the referenced drawings and/or tables, is presented to enable one of ordinary skill in the art to make and use the invention. Various modifications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore, it should be noted that unless explicitly stated otherwise, the figures included herein are illustrated qualitatively and without any specific scale, and are intended to generally present the concept of the present invention.

Definitions

The following definitions are intended to provide the reader with a general understanding of the meaning of the terms, but are not intended to convey the entire scope of each term. Rather, the definitions are intended to supplement the specification and more clearly explain the terms.

16S rDNA—The term "16S rDNA" refers to codes for a small subunit of ribosomal RNA. The 16S rDNA is a widely used informational macromolecule for bacterial systematic studies at the family, genus, species, and subspecies levels. The 16S rDNA contains several conserved sequences that can be used to infer natural relationships between distantly related species and several variable regions that can be used to separate closely related ones.

DNA fingerprinting—The term "DNA fingerprinting" refers to a technique employed to identify an organism on the basis of its DNA profile. Typically, PCR-based molecular techniques are performed. Repetitive-element PCR uses primers complementary to naturally occurring, highly conserved, repetitive DNA sequences. These noncoding sequences are present in multiple copies in the genomes of most Gram-negative and several Gram-positive bacteria. Examples of theses repetitive elements are the enterobacterial repetitive intergenic consensus (ERIC) sequences and the polytrinucleotide $(GTG)_5$ sequence.

Gram-positive—The term "Gram-positive" refers to bacteria that are stained dark blue or violet by Gram staining (crystal violet), in contrast to Gram-negative bacteria which cannot retain the crystal violet stain and instead take up the counterstain (safranin or fuchsine) thus appearing red or pink. Gram-positive organisms are able to retain the crystal violet stain because of a higher amount of peptidoglycan in the inner cell wall and typically lack the secondary or outer wall and lipopolysaccharide layer found in Gram-negative bacteria.

Probiotic—The term "probiotic" refers to bacteria that form at least a part of the transient or endogenous flora and thereby exhibit a beneficial prophylactic and/or therapeutic effect on the host organism. Probiotics are generally known to be safe by those skilled in the art. Although not wishing to be bound by any particular mechanism, the prophylactic and/or therapeutic effect of a spore forming bacterium of this invention results from competitive exclusion of pathogen binding sites, competitive inhibition of growth of pathogens due to superior colonization, parasitism of undesirable microorganisms, production of organic and carboxylic acid and/or production of other extracellular products having antimicrobial activity, or combinations thereof. Typically, probiotics are used to prevent the emergence of a colonic or systemic disease, as opposed to most drugs which are used to cure a disease. These colonic or intestinal pathologies include antibiotic associated colitis, inflammatory bowel diseases (IBS) such as ulcerative colitis and Crohn's disease, colorectal cancer, necrotizing enterocolitis and ileocecitis. The systemic disorders include gut origin septicemia, pancreatitis and multiple organ system failure.

Prebiotic—The term "prebiotic" refers to non-digestible food ingredients that stimulate the growth and/or activity of bacteria in the digestive system which are beneficial to the health of the body. Typically, prebiotics are carbohydrates (such as non-starch polysaccharides, oligosaccharides, sugar acids and alcohols) but the definition also includes non-carbohydrates (such as lignin and glycoproteins). The prebiotic definition does not emphasize a specific bacterial group. Generally, a prebiotic can increase the number and/or activity of groups of bacteria that have several beneficial effects on the host, especially in terms of improving digestion (including enhancing mineral absorption) and the effectiveness and intrinsic stimulation of the immune system.

Synbiotic—The term "synbiotic" refers to nutritional supplements combining live probiotic microorganisms and specific prebiotic substrates in a form of synergism. This can selectively stimulate the growth and/or activate the metabolism of one or more health promoting bacteria and thus improve host welfare.

Functional food—The term "functional food" is a food having a health-promoting or disease-preventing property beyond the basic function of supplying nutrients. Functional foods include foods fortified with health-promoting additives, like "vitamin-enriched" products, and foods with live probiotic cultures and/or prebiotic ingredients.

Introduction

This specification describes *Bacillus subtilis* strains isolated from the pericarp of nixtamalized whole corn. The *Bacillus* strains isolated and described herein were characterized based in part on a polyphasic taxonomic approach that examined their phenotypic and genotypic affiliations. It is readily apparent to those skilled in the art that within nature, various modifications and variations occur to any given organism and that the description described herein may be altered to account for any of these modifications or variations.

The *Bacillus subtilis* strain Maseca-1 has been deposited in an international depository, under conditions that assure that access to the culture will be available during the pendency of this patent application to one determined by the Commissioner of Patents and Trademarks to be entitled thereto under 37 C.F.R. 1.14 and 35 U.S.C. 122. The *Bacillus* Maseca-1 strain disclosed in this description has been deposited in the American Type Culture Collection (ATCC), 10801 University Blvd., Manassas, Va. 20110 USA, as PTA-8831. The deposit was received by the ATCC on Dec. 12, 2007 and was given an accession number by the International Depository Authority of PTA-8831. The deposit has been made to and received by the International Depository Authority under the provisions of the Budapest Treaty, and all restrictions upon public access to the deposit will be irrevocably removed upon the grant of a patent on this application. The deposits will be available as required by foreign patent laws in countries wherein counterparts of the subject application, or its progeny, are filed. It should be understood, however, that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested due to the condition of the deposit(s).

Methods

The methods for collection, isolation and characterization described herein are for illustrative purposes only. It is understood that the species *B. subtilis* may be collected and isolated from any surface where the bacteria is present and that there may be other techniques for characterizing the species. The following techniques are non-limiting examples for completing the described process or technique.

Sample Preparation and Isolation

The *Bacillus subtilis* Maseca strains were isolated from the pericarp of nixtamalized whole corn that had been grown in Amarillo, Tex. and in Chihuahua, Mexico. Four strains were initially isolated and designated Maseca-1, Maseca-2, Maseca-3 and Maseca-4.

The nixtamalization process (lime-cooking) occurs, for example, when the corn is cooked at 80° C.-90° C. in a lime solution (>0.2% calcium hydroxide) for 20-40 minutes, steeped back and washed to ambient temperatures, milled and then dried to make nixtamalized whole-corn flour or masa flour (e.g., MASECA® brand flour). Steeping is used to describe the tempering or hydrating process (e.g., 30%-40% moisture) that occurs when industrial alkali-cooked corn (nixtamal) is allowed to cool to ambient conditions (e.g., 60-150 minutes at 35° C.-40° C.) and the objective is not the separation of starch from the corn as in the industrial wet-milling operation. On the other hand, starch production involves acid processing (e.g., sulfur dioxide) and lactic fermentation (e.g., endogenous *Lactobacillus* spp.) during steeping or soaking whole corn kernels counter-currently (e.g., 24-48 hours, 45° C.-50° C. and 50%-65% moisture). The main result is a dispersion of endosperm protein/zein and starch release during subsequent wet milling and fractionation of germ and pericarp with as little loss of endosperm as possible before its final drying.

An endogenous and endophyte bacterial strain was identified from industrial nixtamalized whole-corn pericarp and plated in nutrient agar at 30° C.-35° C. (pH 6.5-7.5) for 18-24 hours. Representative colonies from agar plates were Gram stained and microscopically examined to determine the strain morphology and motility. Colonies were also streaked onto nutrient agar slant, incubated at 35° C. for 24 h and stored at 5° C. Isolates were selected, purified, and stored in a glycerol solution at −25° C. to −80° C.

Biochemical tests were performed to putatively identify the isolated strains. The API® 50 CHB/E and API® M (motility) media (BIOMERIEUX®) were used to identify the isolated bacterial strains as approximately 98% identical to *Bacillus subtilis* with positive swarming mobility.

Microscopy

FIG. 1 illustrates a light microscope image of the *Bacillus subtilis* Maseca-1 vegetative cells. Strain Maseca-1 is a Gram-positive, rod-shaped, aerobic and facultative, spore forming bacterium.

The isolated bacterium is a motile and long-rod shaped organism (3 to 5 μm by 0.5 to 1 μm). Representative colonies stained with 5% malachite green solution showed an ellipsoidal endospore that stained green while the remainder of the cell stained light red. The endospore can be formed with nutritional stress (e.g., stationary growth). The bacterium is capable of surface swarming through the production of flagella and has the ability to excrete biofilms and exopolymeric substances.

Growth

The *Bacillus subtilis* Maseca strains can be cultured in a liquid or solid medium containing carbon sources, nitrogen sources, inorganic matter, and the like commonly employed in media for culturing microorganisms. Any carbon source may be used, so long as it can be metabolized by *Bacillus subtilis*, for example, glucose, fructose, sucrose, starch, corn steep liquor, alkaline steep liquor, and molasses. Examples of the nitrogen source include peptone, casein hydrolyzate, meat extract, corn steep liquor, alkaline steep liquor and ammonium sulfate. If necessary, the medium may further contain phosphoric acid, salts of potassium, magnesium, calcium, sodium, iron, manganese and the like, vitamins, amino acids, surfactant, and the like. It is preferred to perform the culture aerobically to inhibit growth of anaerobic organisms such as endospore-forming clostridia. With respect to the culture condition, a liquid medium contained in a jar-fermentor under aeration/agitation (e.g., liquid solid fermentation—LSF), a solid medium of the plate-type (e.g., solid substrate fermentation—SSF) or an automated koji-producing fermentor, can be used. Culturing is performed at a temperature of about 25° C. to 42° C., preferably about 32° C. to 40° C., for 12 hours to about 3 days at a culture pH of 5 to 9, preferably a pH of 6 to 8.

Identification of the purified Maseca strains was accomplished by repetitive-sequence-based PCR typing genomic DNA fingerprinting and by ribosomal deoxyribonucleic acid (rDNA) sequencing.

DNA Fingerprinting

Genomic DNA was isolated from Maseca strains 1-4. Polymerase chain reaction (PCR) amplifications were performed on the DNA using primers for (GTG)5-PCR and ERIC-PCR. The PCR products were size separated by electrophoresis in an agarose gel, and the gels were stained with ethidium bromide and digitally captured under UV light. The gel images were visually compared and analyzed.

Figure 2A:
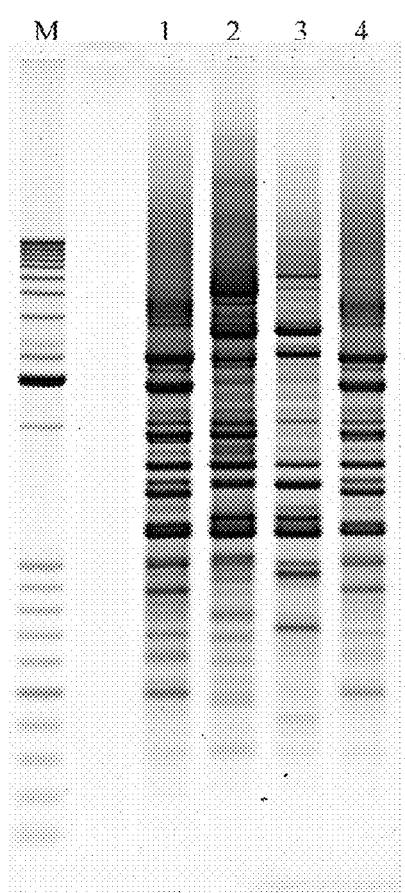
FIGS. 2A and 2B illustrate genomic DNA fingerprint analysis of *Bacillus subtilis* Maseca strains 1-4. The fingerprint patterns are from (GTG)5-PCR in FIG. 2A and ERIC-PCR in FIG. 2B.
Figure 2B:
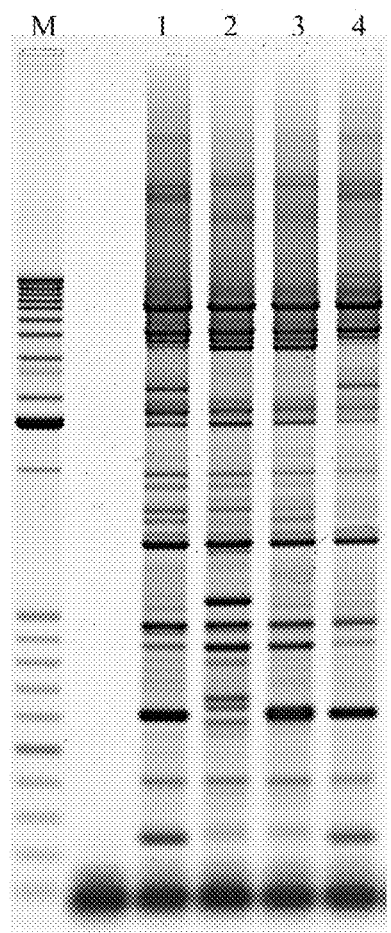

FIG. 2 illustrates a genomic DNA fingerprint analysis of the *Bacillus subtilis* Maseca strains. In FIG. 2-A, the fingerprint patterns from (GTG)5-PCR are shown; in FIG. 2-B, the fingerprint patterns from ERIC-PCR are shown. Lanes 1-4 correspond to Maseca 1-4 respectively. M is a DNA molecular weight marker.

Maseca 1 and Maseca 4 have the same genomic DNA fingerprint pattern from both the (GTG)5-PCR and ERIC-PCR procedures and were identified as the same organism.

16 S rDNA Sequencing

Genomic DNA from liquid cultures was used as a template for PCR amplification. Purified amplicons were sequenced and the identity of a given PCR product was verified by sequence analysis. The phylogenetic relationships of organisms covered in this description were determined by comparison of the individual 16S rDNA sequences to existing sequences in public databases, such as the database of the National Center for Biotechnology Information (NCBI). Evolutionary trees based on distance and maximum-likelihood analyses were constructed with Phylogenetic trees (dendograms) using Neighbor-Joining (NJ) and Unweighted Pair Group Method Arithmetic Mean (UPGMA) methods. Bootstrap methods were used to provide confidence estimates for tree topology in the NJ method.

Figure 3:
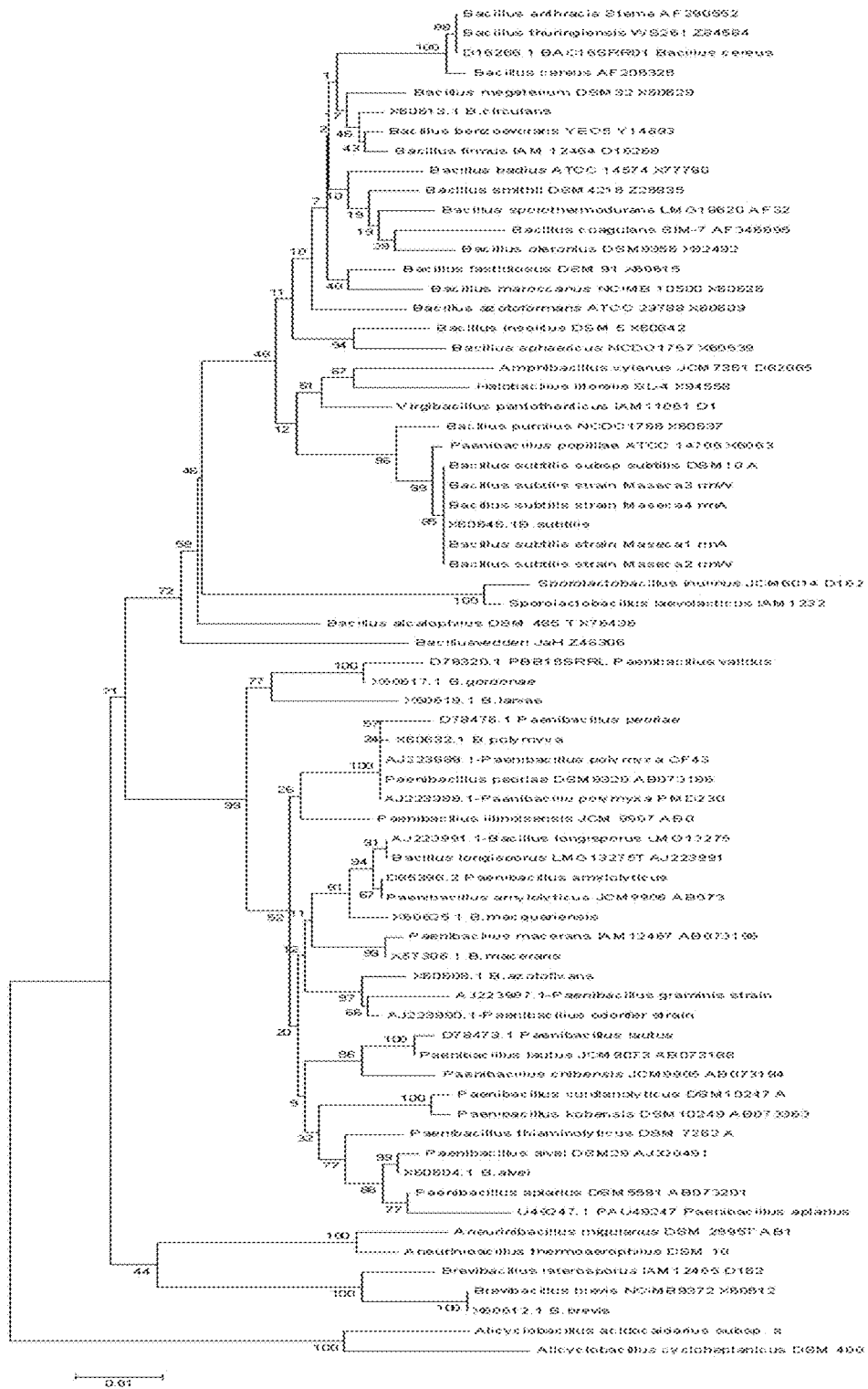
FIG. 3 is a chart illustrating a phylogenetic tree of *Bacillus* spp. and other species closely related to Maseca 1-4 strains based on maximum likelihood analysis of 16S rDNA nucleotide sequences.

The resulting analyses indicated that the Maseca strains 1-4 were most closely related to members of the species group *Bacillus subtilis* subsp. *subtilis* (a variant of strain 168, strain ATCC9799, strain DSM10A or ATCC6051). A representative maximum-likelihood phylogenetic tree based on 16S rDNA sequences of several straight-rod and spore-forming bacteria is shown in FIG. 3. Strain number and GenBank database accession numbers (e.g., AL009126) are shown. Numbers are percentage bootstrap or sequence identity values (e.g., 85±0.01) of that branch of the tree.

As such, the present invention relates to isolated biologically pure cultures of bacteria isolated from the pericarp of nixtamalized whole corn. In particular, the bacteria are *Bacillus subtilis* and more particular, *Bacillus subtilis* Maseca-1, deposited as ATCC accession number PTA-8831.

As a species, *Bacillus subtilis* is a Gram positive, non-pathogenic, spore-forming organism normally found in the rhizosphere of soil, in and around plant roots (e.g., maize and wheat) and within the gastrointestinal tract of animals and humans. The organism is aerobic and facultative, grown typically in nutrient broth (e.g., NB medium) at about 32° C. to about 40° C. The organism can be induced to sporulate when grown in sporulation medium (e.g., Luria-Bertani or DSM medium), which induces spore formation by nutrient exhaustion. The tough, protective endospore allows the organism to tolerate extreme environmental conditions. *B. subtilis* is non-pathogenic and is generally regarded as safe (i.e., GRAS classification by the U.S. Food and Drug Administration) or as qualified presumption of safety (i.e., QPS status by the European Commission-SCAN, 2003).

Characterization of Culture Supernatant

Characterization of the biomolecules present in the spent culture supernatant of Maseca-1 was performed. Metabolomic analysis of lantibiotic peptides, EPS-exopolysaccharides (e.g., levan and dextran), organic acids and protease analysis was carried out.

To produce the samples, Maseca-1 cultures were incubated in nutrient broth (NB) or in Luria-Bertani media (LB) at 35° C., pH 6.8 with vigorous orbital shaking (200 rpm) for 24-48 hours. The cultured media was centrifuged (4000 rpm for 20 min.) to remove the cells and the cell free supernatant was then fractionated using an Amicon® Centricon® membrane filter (MILLIPORE™).

In Sample 1 and Sample 2, the supernatant was fractionated with a membrane filter having a molecular weight cut-off of 3000 Daltons. Two fractions were produced, a top retentate (FHMW) that could not pass through the membrane, corresponding to material greater than 3000 Daltons, and a bottom filtrate (FLMW) fraction corresponding to low molecular weight material less than 3000 Daltons. The FHMW and FLMW fractions were stored frozen at −80° C.

In Sample 3, the supernatant was double filtered, first using an Amicon® Centricon® BioMax PB membrane filter (MILLIPORE™) with a molecular weight cut-off of 8000 Daltons. The bottom filtrate fraction corresponding to material of less than 8000 Daltons was further filtered using a membrane filter with a molecular weight cut-off of 3000 Daltons. Two fractions were produced, the top retentate (FHMW) corresponding to material of 3000-8000 Daltons, and the bottom filtrate (FLMW) corresponding to material less than 3000 Daltons. The FHMW material was further processed to extract lantibiotic peptides through organic solvent extraction.

Organic Solvent Extraction

Twenty-five (25) ml of FHMW fraction from Sample 3 was extracted with 12.5 ml of chloroform for about 20 minutes. This produced a brown milky mix. This solution was ultracentrifuged at 10,400 g for 20 minutes at 12° C. Multiple layers were obtained, the upper layer corresponding to the organic (chloroform) portion, the bottom aqueous layer, and a middle precipitate layer floating between the aqueous and organic phases, corresponding to the lantibiotic peptide mix. This precipitate was removed and dried overnight. The total amount of wet pellet obtained from 25 ml of filtrate was 975 mg. After drying, the pellet was suspended in 2.5 ml of 0.1M Tris buffer, pH 7.0. An aliquot of this organic extracted crude fraction (OECF) was removed. The remaining 2.1 ml was suspended in 50 ml of nanopure molecular biology quality water and stored frozen at −80° C.

Analysis for Lantibiotic Peptides

Samples of spent culture supernatant (i.e., Samples 1, 2 and 3) were analyzed by liquid chromatography-mass spectrometry (LC-MS) for the presence of lantibiotic peptides (e.g., nisin A, nisin B, subtilin, mutacin, epidermin). LC-MS analysis was carried out on a Finnigan LTQ Orbitrap™ system (Thermo Electron Corp.). MS detection was carried out using electrospray ionization (ESI) in the positive mode using a Full MS scan event from m/z 200-2000. Separations were carried out in the reversed phase mode on a ProSphere™ C4 300 Å column 150×3.2mm, 5 µm (Grace Alltech). All separations were carried out using a water to acetonitrile mobile phase with 0.1% formic acid. Different gradients were tested.

HPLC conditions and the selected gradients were as follows:
Solvent A: MilliQ water+0.1% formic acid
Solvent B: Acetonitrile+0.1% formic acid
Flow rate: 400 µl/min (split before MS)
Column Temperature: 30° C.
Injection volume: 10 µl
Gradient: linear

| Time (min) | % A | % B |
|---|---|---|
| 0 | 95 | 5 |
| 2 | 95 | 5 |
| 50 | 10 | 90 |
| 55 | 10 | 90 |
| 55.5 | 95 | 5 |
| 60 | 95 | 5 |

Figure 4A:
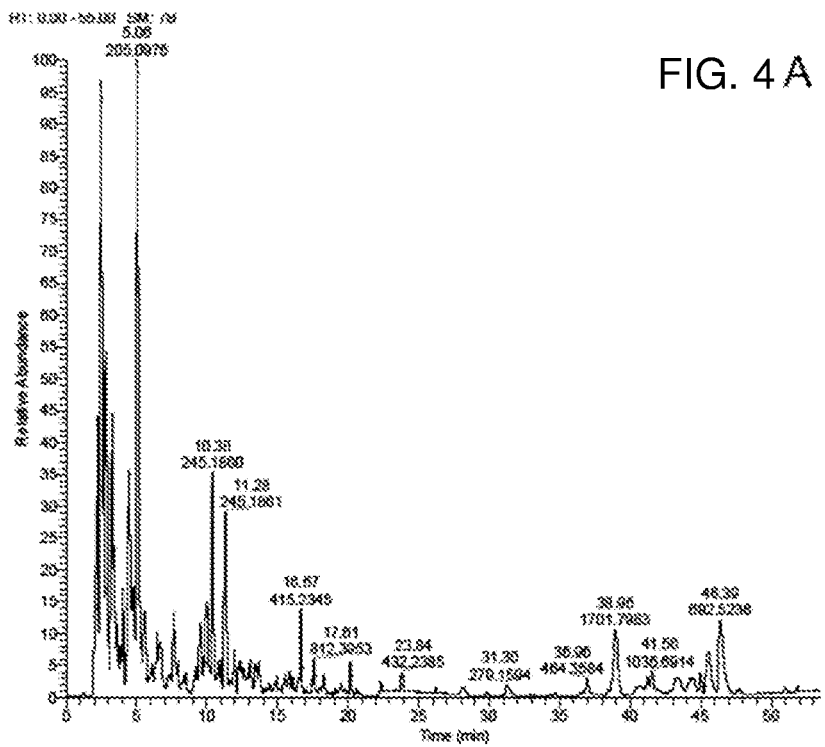
FIGS. 4A, 4B, 4C and 4D are base peak LC-MS chromatograms of *Bacillus subtilis* Maseca-1 sample supernatant (A-C) and a nisin standard (D).
Figure 4B:
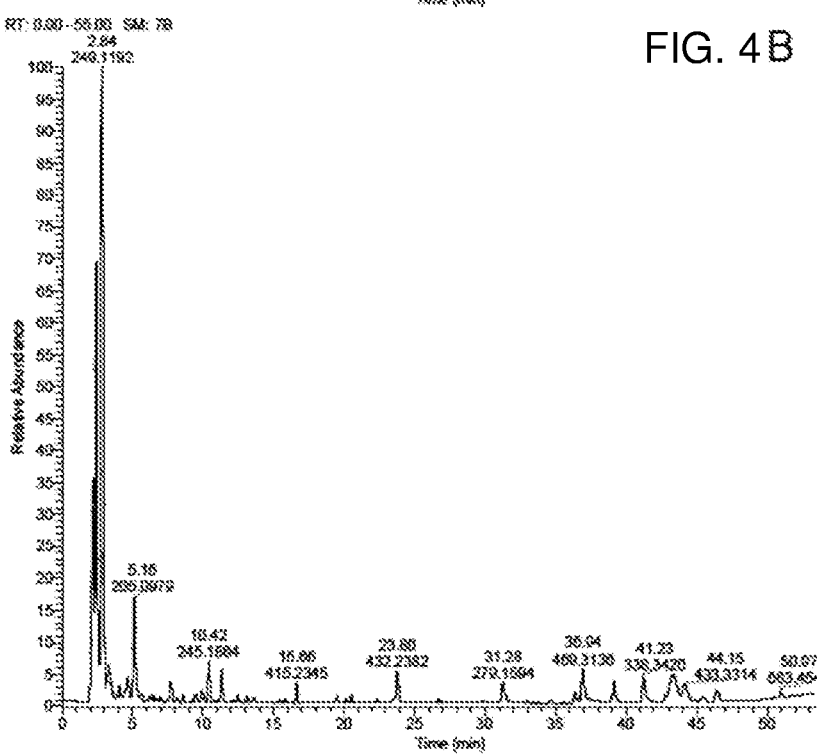
Figure 4:
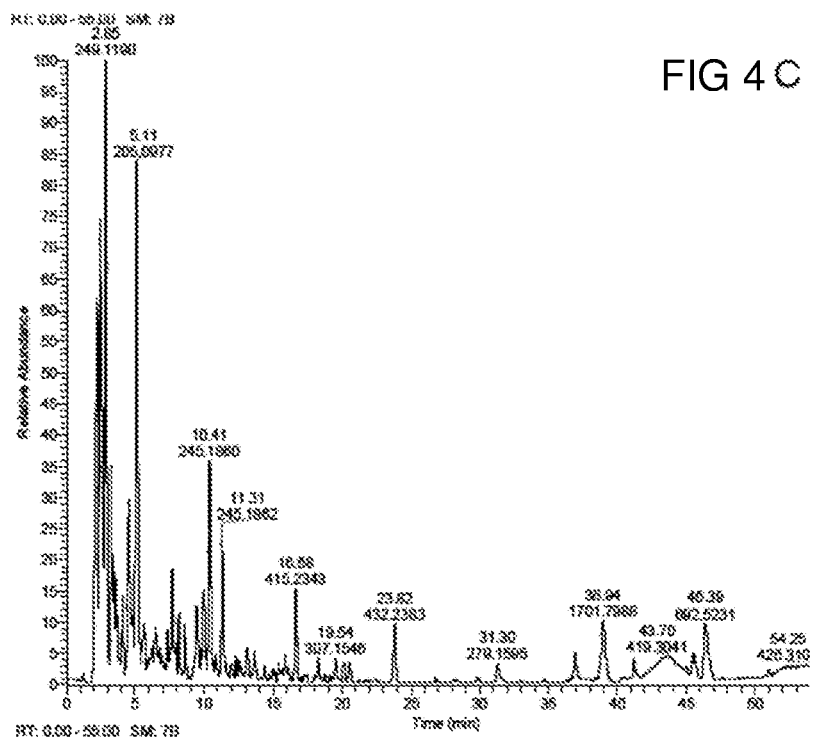

The resulting base peak LC-MS chromatograms of the three samples (Samples 1, 2 and 3) are shown in FIGS. 4A, 4B and 4C, along with a nisin standard in FIG. 4D (Sigma N5764, Sigma-Aldrich®). The three samples showed relatively similar patterns of peaks, i.e., high density peaks with high intensity at short retention time and some lower abundant peaks at high retention times. As can be seen from the figures, several peaks were detected but none of them could be assigned to nisin.

Figures 5A, 5B:
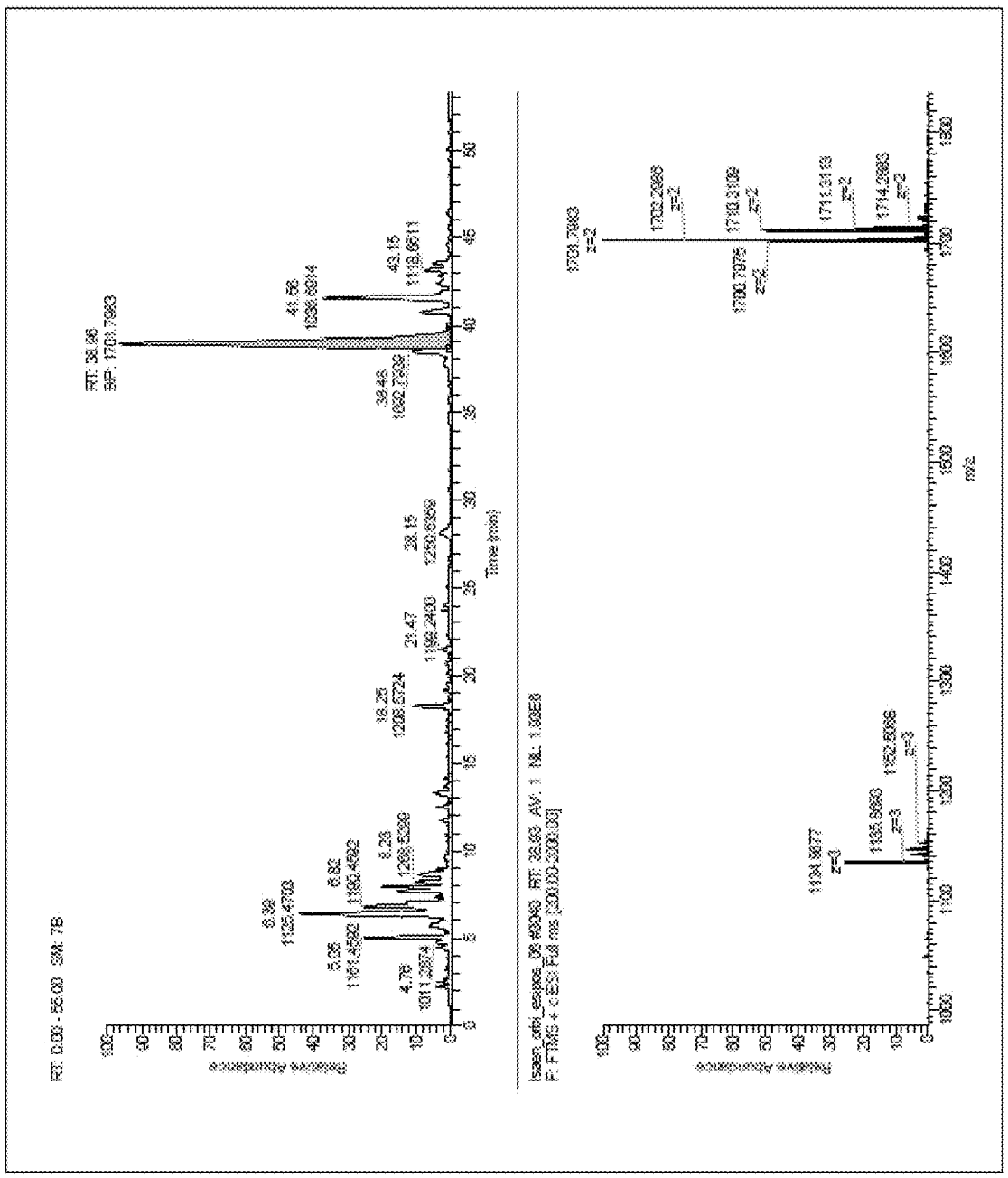
FIG. 5A is a base peak LC-MS chromatogram of *Bacillus subtilis* Maseca-1 sample supernatant showing a peak at m/z 1701.8.
FIG. 5B is a mass spectrum analysis of that peak.

Due to the lack of appropriate reference compounds for mycosubtilin, subtilin, mutacin and epidermin, the LC-MS chromatograms were searched for typical mass to charge (m/z) values (see, Table I). No exact matches could be found with the previously characterized lantibiotics or bacteriosins; however, one peak was observed in all three samples that showed characteristics of a lantibiotic (see, FIG. 5A, peak at RT 38.96 and BP 1701.8). The retention time and mass determined for this peak is in the same range as expected for lantibiotics. Furthermore, the mass spectrum analysis of that peak showed typical multiple-charged hydrogen ions typical for peptides, where double and triple charged ions are the most abundant (see, FIG. 5B). The peak could not be assigned to a specific lantibiotic based on information available in literature. It is known that lantibiotics show some variation with respect to molecular mass depending on the specific lantibiotic and the experimental conditions due to oxidation, methylation or other modifications.

TABLE I

Possible m/z values in ESI positive mode for the lantibiotic peptides

| | | 1+ | 2+ | 3+ | 4+ | 5+ | 6+ |
|---|---|---|---|---|---|---|---|
| Epidermin | H | 2166.6 | 1083.8 | 722.9 | 542.4 | 434.1 | 361.9 |
| MW = | Na | 2188.6 | 1105.8 | 744.9 | 564.4 | 456.1 | 383.9 |
| 2165.6 | H and Na | | 1094.8 | 737.5 | 558.9 | 451.7 | 380.3 |
| | | | | 730.2 | 553.4 | 447.3 | 376.6 |
| | | | | | 547.9 | 442.9 | 372.9 |
| | | | | | | 438.5 | 369.1 |
| | | | | | | | 365.4 |
| Nisin A | H | 3355.0 | 1678.0 | 1119.0 | 839.5 | 671.8 | 560.0 |
| MW = | Na | 3377.0 | 1700.0 | 1141.0 | 861.5 | 693.8 | 582.0 |
| 3354 | H and Na | | 1689.0 | 1133.7 | 856.0 | 689.4 | 578.3 |
| | | | 1126.3 | 850.5 | 685.0 | 574.7 |
| | | | | | 845.0 | 680.6 | 571.0 |
| | | | | | | 676.2 | 567.2 |
| | | | | | | | 563.5 |
| Nisin Q | H | 3328.0 | 1564.5 | 1110.0 | 832.8 | 666.4 | 555.5 |
| MW = | Na | 3350.0 | 1686.5 | 1132.0 | 854.8 | 688.4 | 577.5 |
| 3327 | H and Na | | 1675.5 | 1124.7 | 849.3 | 684.0 | 537.8 |
| | | | | 1117.3 | 843.8 | 679.6 | 570.2 |
| | | | | | 838.3 | 675.2 | 566.5 |
| | | | | | | 670.8 | 562.7 |
| | | | | | | | 559.0 |
| Nisin Z | H | 3332.0 | 1666.5 | 1111.3 | 833.8 | 667.2 | 556.2 |
| MW = | Na | 3354.0 | 1688.5 | 1133.3 | 855.8 | 689.2 | 578.2 |

TABLE I-continued

Possible m/z values in ESI positive mode for the lantibiotic peptides

| | | 1+ | 2+ | 3+ | 4+ | 5+ | 6+ |
|---|---|---|---|---|---|---|---|
| 3331 | H and Na | | 1677.5 | 1126.0 | 850.3 | 684.8 | 574.5 |
| | | | | 1118.7 | 844.8 | 680.4 | 570.8 |
| | | | | | 839.3 | 676.0 | 567.2 |
| | | | | | | 671.6 | 563.3 |
| | | | | | | | 559.7 |
| Mutacin I | H | 2365.0 | 1183.0 | 789.0 | 592.0 | 473.8 | 395.0 |
| MW = | Na | 2387.0 | 1205.0 | 611.0 | 614.0 | 495.8 | 417.0 |
| 2364 | H and Na | | 1194.0 | 803.7 | 608.5 | 491.4 | 413.3 |
| | | | | 796.3 | 603.0 | 487.0 | 409.7 |
| | | | | | 597.5 | 482.6 | 406.0 |
| | | | | | | 478.2 | 402.2 |
| | | | | | | | 398.5 |
| Mutacin | H | 2264.0 | 1132.6 | 755.3 | 566.8 | 453.6 | 378.2 |
| 1140 | Na | 2286.0 | 1164.6 | 777.3 | 688.8 | 475.6 | 400.2 |
| MW = | H and Na | | 1143.5 | 770.0 | 583.3 | 471.2 | 396.5 |
| 2263 | | | | 762.7 | 577.8 | 466.8 | 392.8 |
| | | | | | 572.3 | 462.4 | 389.2 |
| | | | | | | 458.0 | 385.3 |
| | | | | | | | 381.7 |
| Mutacin | H | 2271.0 | 1136.0 | 757.7 | 568.5 | 455.0 | 379.3 |
| B-Ny255 | Na | 2293.0 | 1158.0 | 779.7 | 590.5 | 477.0 | 401.3 |
| MW = | H and Na | | 1147.0 | 772.3 | 585.0 | 472.6 | 397.7 |
| 2270 | | | | 765.0 | 579.5 | 468.2 | 394.0 |
| | | | | | 574.0 | 463.8 | 390.3 |
| | | | | | | 459.4 | 388.5 |
| | | | | | | | 382.8 |
| Subtilin | H | 3322.0 | 1661.5 | 1108.0 | 831.3 | 665.2 | 554.5 |
| MW = | Na | 3344.0 | 1683.5 | 1130.0 | 853.3 | 687.2 | 576.5 |
| 3321 | H and Na | | 1672.5 | 1122.7 | 847.8 | 682.8 | 572.6 |
| | | | | 1115.3 | 842.3 | 878.4 | 569.2 |
| | | | | | 836.8 | 674.0 | 565.5 |
| | | | | | | 669.6 | 561.7 |
| | | | | | | | 558.0 |

Analysis of Exopolysaccharide (EPS) To prepare the samples for exopolysaccharide analysis, the supernatant fractions were extracted with ethanol and the EPS was precipitated. The FHMW and FLMW fractions were combined and ice cold ethanol (1.5 times sample volume) was added to the sample. The samples were mixed gently for 5 minutes. As soon as the mixing process ended, the formation of white EPS precipitate began to aggregate on the top layer and gradually precipitated and deposited on the bottom of the container. The solution was placed overnight at −20° C. and allowed to continue to precipitate. Then, the clear ethanol phase on top was carefully removed and the precipitated EPS collected by further centrifugation (9000 rpm for 15 min).

For fructose determination, the pellet containing the EPS was incubated with 2 M trifluoroacetic acid for 2 hours. Under these conditions, fructose monomers are fully released from the EPS. For glucose determination, the pellet containing EPS was incubated with 2 M sulphuric acid for 1 hour at 100° C. Under these conditions, glucose monomers are fully released from the EPS. Subsequently, the samples were diluted and analyzed using High Performance Anion Exchange Chromatography with Pulsed Amperometric Detection (HPAEC-PAD). Inulin treated with trifluoroacetic acid, potato starch treated with sulphuric acid and EPS from LB 180 treated with sulphuric acid were included as quality controls for hydrolysis.

Figure 6A:
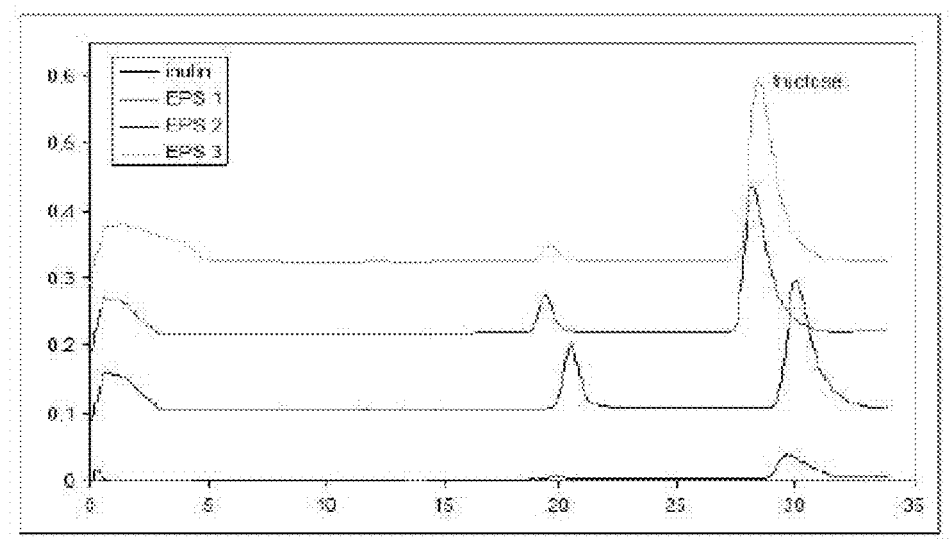
FIGS. 6A and 6B are High Performance Anion Exchange Chromatography with Pulsed Amperometric Detection (HPAEC-PAD) chromatograms of *Bacillus subtilis* Maseca-1 samples for fructose from fructosylpolymer or levan (6A) and glucose from glucosylpolymer or dextran (6B).
Figure 6B:
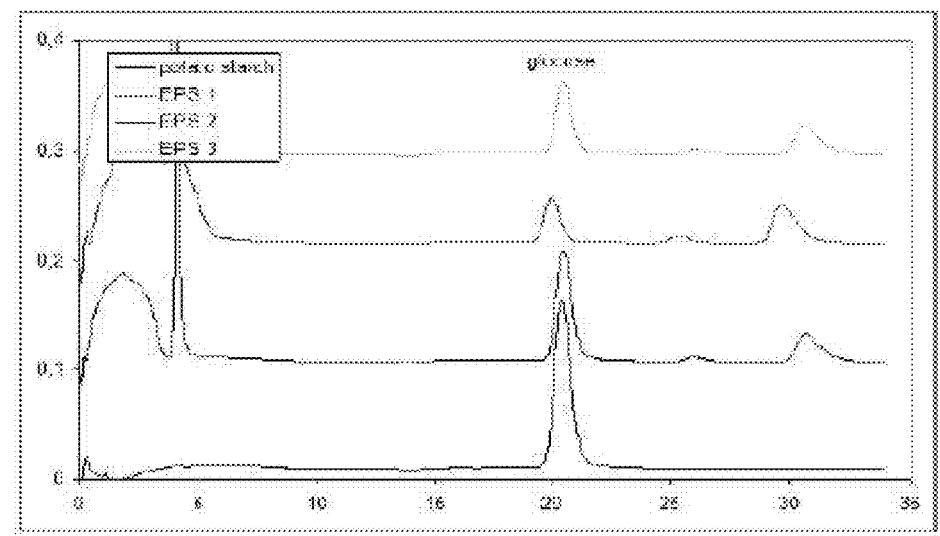

The EPS prepared from Samples 1, 2 and 3 were analyzed and the HPAEC-PAD chromatograms for fructose and glucose are shown in FIG. 6A and FIG. 6B, respectively. As can be seen from the chromatograms, the retention time of the monomer can differ due to the pH of the hydrolyzed sample.

The results are also shown in Table II. The fructose/glucose ratio is based on peak areas of the chromatograms.

TABLE II

| Sample number | Ratio fructose/glucose |
|---|---|
| 1 | 5 |
| 2 | 20 |
| 3 | 10 |

Analysis for Protease Enzyme Activity

Extracellular proteolytic activity was measured according to a modified procedure as described by Holm, K. A. (Automated colorimetric determination of acid proteinase activity in fermentation samples using a trinitrobenzenesulphonic acid reagent. (1980) *Analyst*, 105:18-24).

The procedure was fully automated using a Cobas Mira Plus auto-analyzer. Proteolytic activity of culture supernatants was determined by incubating samples with 0.5% (w/v) N,N-dimethylated base in 0.25 M MES buffer (pH 6) for 17.5 min at 37° C. As a blank, samples were incubated without N,N-dimethylated casein. The reaction was stopped by the addition of a solution containing 0.5 g $Na_2SO_3$ $l^{-1}$ in 0.1 M borate buffer at pH 9.3. Simultaneously, 2,4,6,-trinitrobenzene sulfonic acid (TNBSA) was added. TNBSA reacts with the free amino acid groups resulting in a yellow color, which was measured at 405 nm after 3 min. Glycine was used as standard. One unit of protease activity was defined as the amount of enzyme which in 1 min under the given standard conditions produces absorption at 405 nm equal to 1 µM glycine.

The results of the protease activity for the three samples are given in Table III.

TABLE III

| Sample | Sample pH | Protease activity - mmol $L^{-1}$ $min^{-1}$ (pH 6) |
|---|---|---|
| 1 | 5.81 | 0 |
| 2 | 6.78 | 0.003 |
| 3 | 6.31 | 0.01 |

As shown in Table III, no or very low protease activity was measured. The samples contained a high background of free or primary bound ammonia. Accordingly, the protease samples were diluted 3-4 times to lower the background to an acceptable level. The protease activity end-result was the same for the diluted samples; therefore the dilution did not have any effect on the protease activity.

Analysis for the Presence of Short-chain Fatty Acids

Compounds were detected by HPLC coupled to ultraviolet UV and refractive index RI detection using an organic acid column (Aminex®, BIO-RAD) with an isocratic flow of acidic water containing $H_2SO_4$. Analysis was carried out on a Waters Alliance 2695 HPLC system coupled to a Waters 996 PDA and 2412 RI detector. The specific short-chain fatty acids were quantified using external calibration curves.

Figure 7:
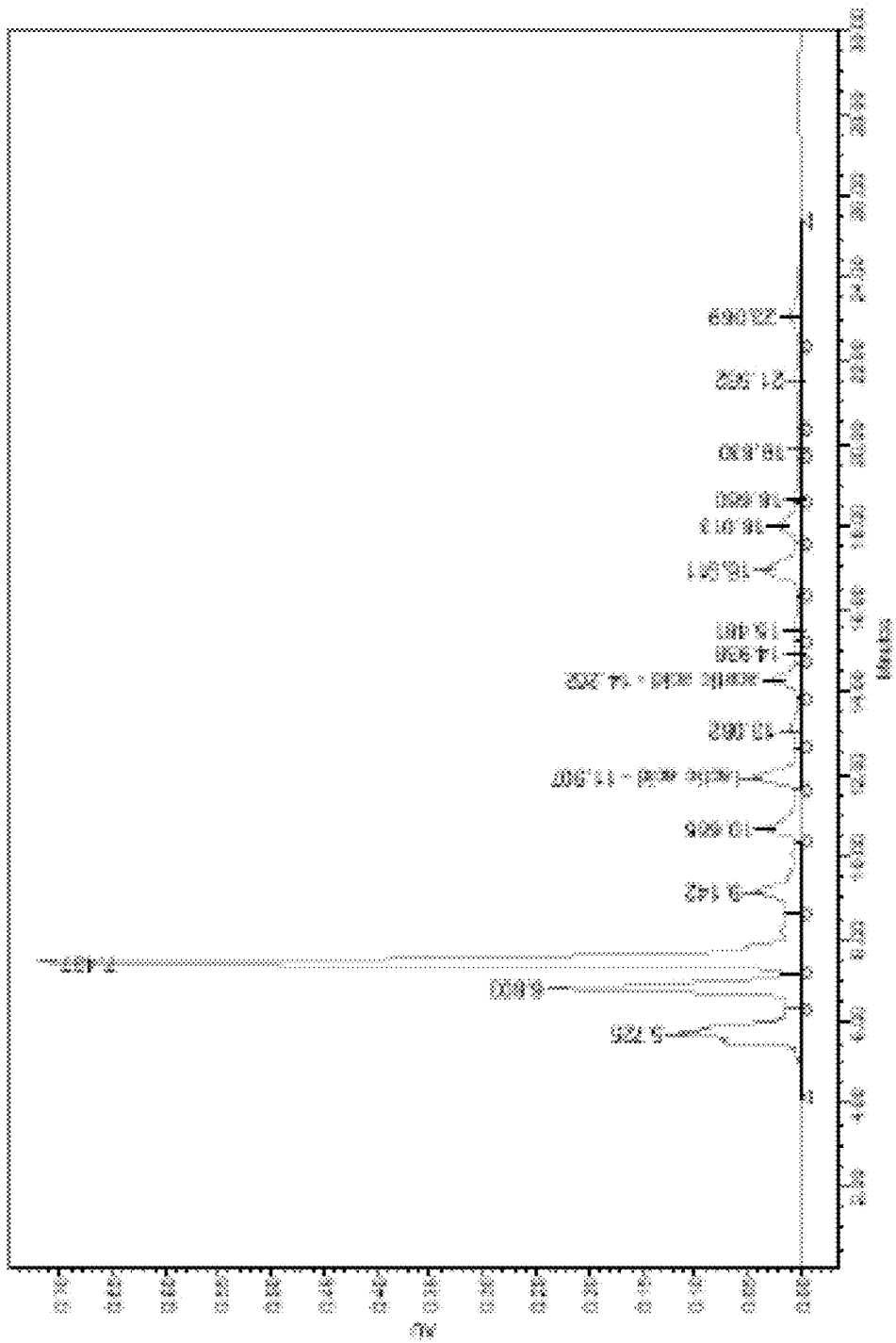
FIG. 7 is chromatogram of short-chain fatty acid HPLC analysis of *Bacillus subtilis* Maseca-1 sample.

FIG. 7 illustrates an exemplary chromatogram of short-chain fatty acid HPLC analysis of Sample 1. Using external calibration curves, the concentration of the specific short-chain fatty acids was determined.

The concentration of short-chain fatty acids as determined by HPLC is given in Table IV.

TABLE IV

| | Short-chain fatty acid concentration | | | | |
|---|---|---|---|---|---|
| Sample | Succinic acid (mg/ml) | Lactic acid (mg/ml) | Acetic acid (mg/ml) | Propionic acid (mg/ml) | Butyric acid (mg/ml) |
| 1 | <0.56[2] | 1.3 | 0.93 | <1.3[4] | <LOD[5] |
| 2 | <LOD[1] | 0.05 | 0.08 | <LOD[3] | <LOD[5] |
| 3 | <0.56[2] | 0.62 | 0.73 | <1.3[4] | <LOD[5] |

[1] Limit of detection (LOD) for succinic acid was 0.02 mg/ml;
[2] due to disturbances the LOD for these samples is 0.56 mg/ml;
[3] LOD for propionic acid was 0.05 mg/ml;
[4] due to disturbances the LOD for these samples is 1.3 mg/ml;
[5] LOD for butyric acid was 0.03 mg/ml The results for short-chain fatty acids show similar concentrations for Samples 1 and 3, but decreased concentrations were found in Sample 2.

Microorganism Growth Inhibition The ability of *Bacillus subtilis* Maseca-1 to inhibit the growth of Gram-positive pathogen *Micrococcus luteus* was analyzed.

A 0.3 ml culture of *M. luteus* (ATCC 9341) was added to 500 ml of molten LB agar, poured into Petri dishes and allowed to solidify. Paper discs (6.0 mm diameter) were loaded with 5 μl of sample and dried. Then, the discs were placed on the agar surface and the plates were incubated overnight at 37° C. Growth inhibition was measured as the diameter of the clear zone around each paper disc. The measurements are taken from duplicate plates (4 disks/plate). The OECF fractions obtained from Sample 3 were tested.

TABLE V

| Growth inhibition of peptide antibiotics from *Bacillus subtilis* Maseca-1 [1, 2] | |
|---|---|
| Inhibition zone of *M. luteus* (mm) OECF 1 | Inhibition zone of *M. luteus* (mm) OECF 2 |
| 18.5 | 19 |
| 19.5 | 18.5 |
| 18 | 20 |
| 17.5 | 19.5 |

[1] Data are means of two repeated trials.
[2] Growth inhibition distances measured as diameter (mm) of the clear zone around disk.

The ability of *Bacillus subtilis* Maseca-1 to inhibit the growth of pathogens *Micrococcus luteus*, *Bacillus cereus* and *Aspergillus flavus* was also analyzed as described above.

TABLE VI

| Growth inhibition of peptide antibiotics from *Bacillus subtilis* Maseca-1 on pathogens [1, 2] | | | | |
|---|---|---|---|---|
| Run | ML | BC | AF | Control |
| 1 | 16.1 | 34.75 | 10.5 | 6.5 |
| 2 | 16.5 | 34.50 | 10.5 | 6.5 |
| 3 | 21.0 | 35.10 | 10.5 | 6.5 |
| 4 | 22.0 | 36.00 | 10.5 | 6.5 |

ML = *Micrococcus luteus* ATCC 9341;
BC = *Bacillus cereus* NRLL;
AF = *Aspergillus flavus* NRLL
[1] Data are means of two repeated trials.
[2] Growth inhibition distances measured as diameter (mm) of the clear zone around disk.

The Maseca-1 isolate demonstrated the ability to secrete peptides that inhibit the growth of pathogenic microorganisms.

The following Example 1 shows the growth, extraction and application of the antimicrobial extract of the *Bacillus subtilis* Maseca-1 isolate in food materials to inhibit unwanted microorganisms in various foods and food materials.

EXAMPLE 1

Growth and Filter Extraction

A sterilized broth flask (tryptic soy and added sucrose with minerals mix adjusted at a pH of 7.1) was inoculated with *Bacillus subtilis* Maseca-1 cells (slant culture) and incubated at 35° C. with orbital shaking (120-160 rpm) during 18 hours as a seed culture. A second growth culture was prepared by transferring seed (10-20% v/v) into another sterilized broth flask and incubated with agitation at 35° C. for 30 hours.

The culture was then centrifuged in a refrigerated centrifuge (4000 rpm, 5° C., 20 min) and the spent cell-free supernatant was mixed with chloroform (1:0.5 v/v) during 30 minutes. This suspension was centrifuged again (9000 rpm, 5° C., 15 min). Three layers were produced and the extracted solids at the interface (amphiphilic compounds) were recovered with a pipette after carefully pouring off the top aqueous layer.

Sterile Tris buffer was used to thoroughly resuspend the extracted pellet and loaded into sterile AMICON ultracentrifuge devices (10,000 Dalton MWCO) and centrifuged (11,000 rpm, 5° C., 15 min) to recover a filtered extract (filtrate <10KDa). The filtered extract (Maseca-1 extract) was mixed with sterile Tris buffer and held under refrigeration (<10° C.).

Shelf-life Study

A shelf-life study was conducted with laboratory corn flour and dough, and corresponding tortillas stored three days at 25° C. in order to measure bacteria and mold counts along with percent inhibition. Three additive formulations with corn flour were tested: control (without additive), with filtered Maseca-1 extract (0.1% to 1% w/w) and with organic acid additive (0.32% w/w).

The organic acid additive is a commercial product containing food grade benzoic acid (0.2% w/w flour), fumaric acid (0.12% w/w flour), and/or sorbic acid (0.05% w/w flour), commonly used in the wheat, corn and tortilla product industry.

All tests used nixtamalized corn flour (MASECA brand). The control dough was manually kneaded for 3 to 5 minutes under sterile conditions by rehydrating the flour with sterile water in a 1:1.25 ratio. In the filtered-extract dough, water was mixed with the filtered extract before kneading, and in the organic acid dough the flour was thoroughly mixed with the organic acids before adding and mixing the sterile water.

Under sterile conditions, doughballs were plated flat and dough disks were cooked on a hot plate (250-290° C.) for about 15 s to cook on each side. The tortilla is turned again a final time and cooked for about 15 s until the evaporated water makes it swell (about 45-48% final moisture content). After cooling, the tortillas were placed inside sterile petri plates and packed in polyethylene bags for storage at 25° C.

For each test, the corn dough (0 days) and corresponding tortillas (0 days and 3 days storage) were examined for the presence of bacteria flora (using plate count agar/PCA for mesophiles) and mold flora (using potato dextrose agar/PDA acidified with tartaric acid for fungi), and the Colony Forming Units per gram (CFU/g) was measured. The microflora inhibition/reduction was calculated as follows:

% inhibition or reduction=(1−CFU with additive/ CFU without additive)×100, where additive refers to either the filtered-extract (extract<10KDa) or the organic acid (commercial), and without additive refers to the control (added water only).

Figure 8A:
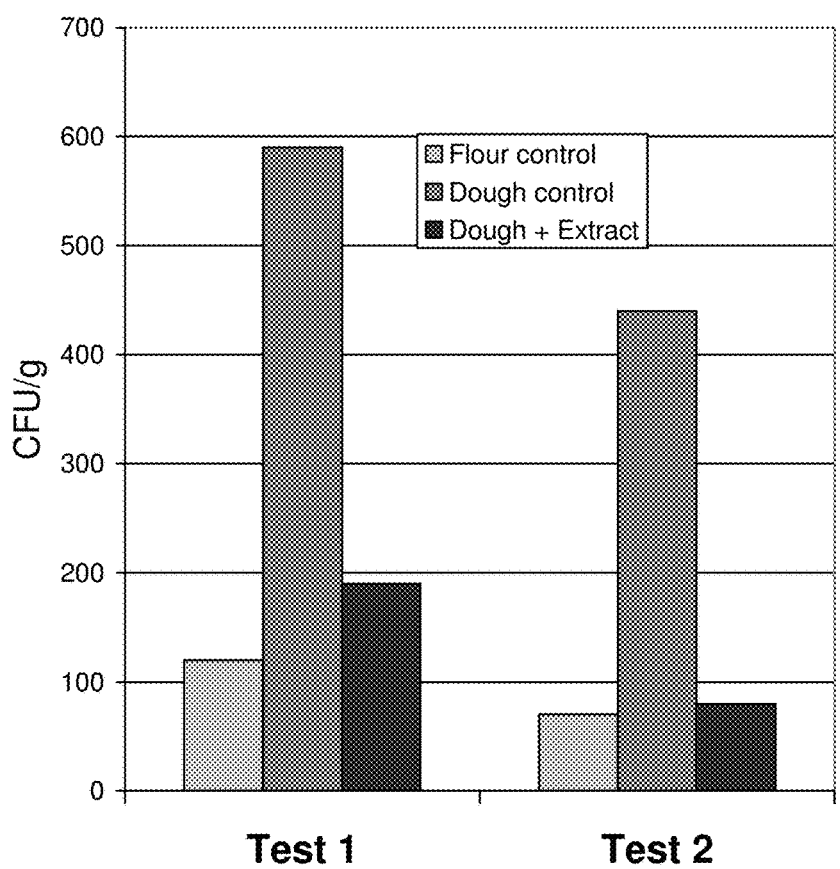
FIGS. 8A and 8B are graphs showing the bacteria and mold counts in nixtamalized corn flour and dough with and without the Maseca-1 extract.

FIG. 8A shows microbial counts in nixtamalized corn flour and dough without additive (control) and with added Maseca-1 extract. Either water (control) or extract was added to the corn flour and dough was prepared. The flour and dough were analyzed for bacteria about 0.5-1.0 hour after the dough was prepared. In two separate experiments, the bacterial counts (CFU/g) were dramatically lower in the dough with added Maseca-1 extract (190, 80) compared to the control dough (590, 440).

Figure 8B:
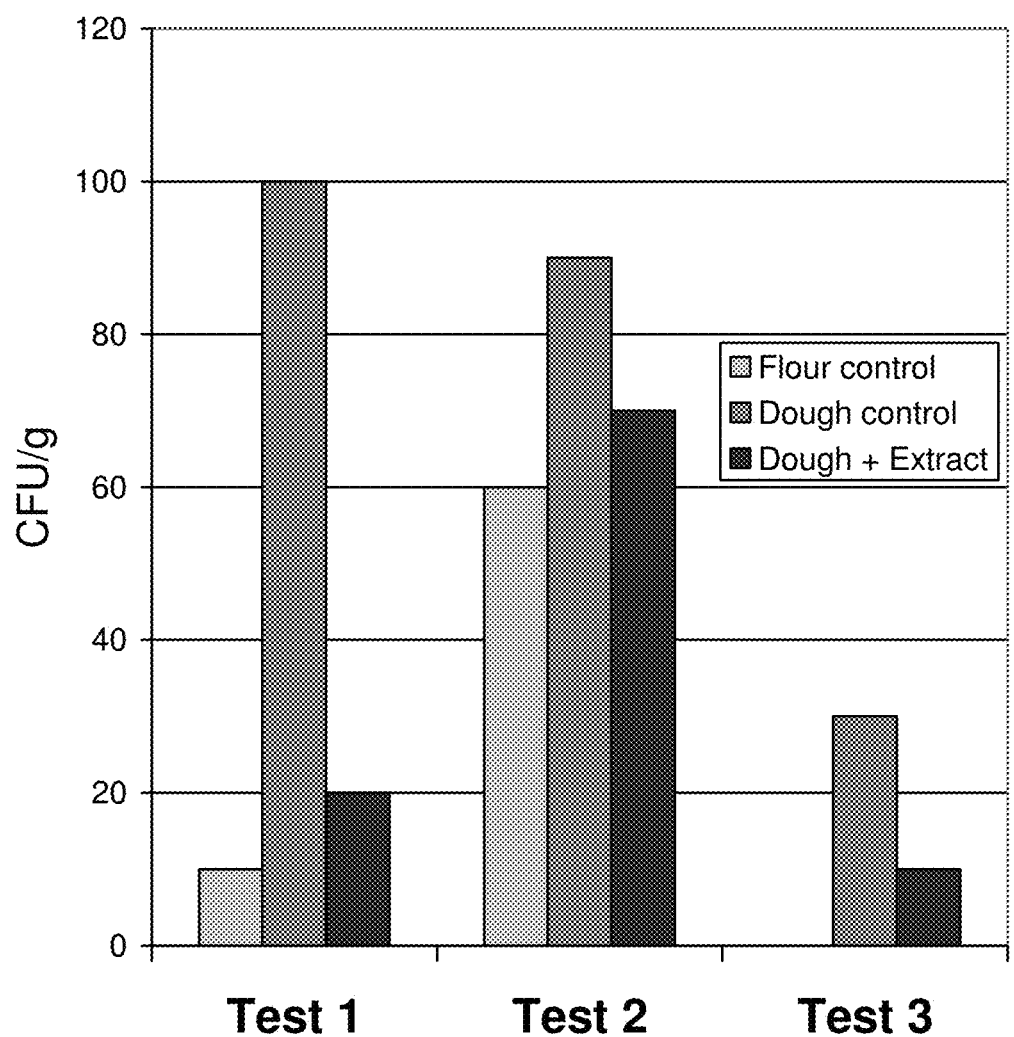

FIG. 8B shows mold counts in nixtamalized corn flour and dough without additive (control) and with added Maseca-1 extract. Either water (control) or extract was added to the corn flour and dough was prepared. The flour and dough were analyzed for mold about 0.5-1.0 hour after the dough was prepared. In three separate experiments, the mold counts (CFU/g) were dramatically lower in the dough with added Maseca-1 extract (20, 70, 10) compared to the control dough (100, 90, 30).

Figure 8C:
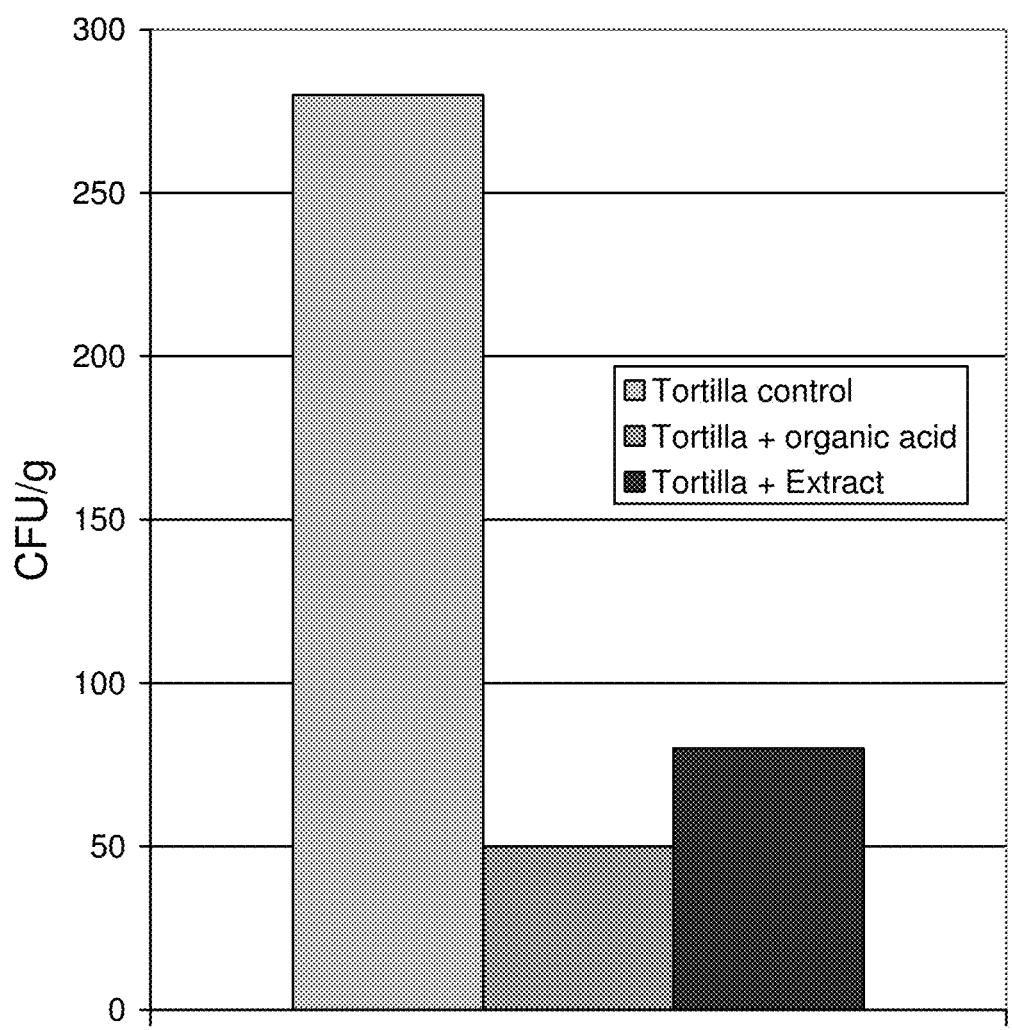
FIGS. 8C and 8D are graphs showing the bacteria counts (CFU/g) in tortillas prepared from nixtamalized corn and dough with no additive (control), added commercial organic acid and added Maseca-1 extract.

FIG. 8C shows bacterial counts in tortilla prepared from nixtamalized corn flour without additive (control), with commercial organic acid, or with Maseca-1 extract. Either water (control), organic acid or extract was added to the flour or dough and tortillas were prepared soon thereafter—about 0.5-1 hours after the dough was prepared. The bacteria counts (CFU/g) were dramatically lower in the tortilla prepared with the added Maseca-1 extract (80) compared to control (280), and were comparable to that of the organic acid (50).

Figure 8D:
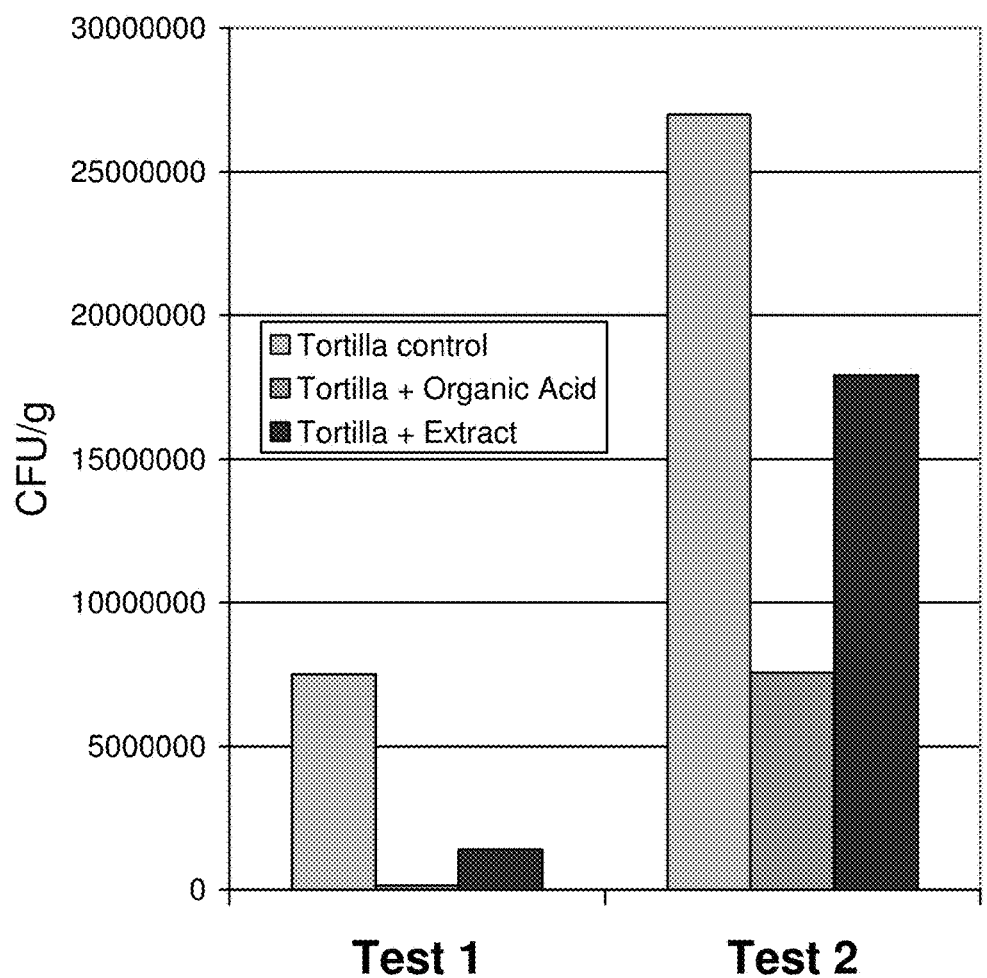

FIG. 8D shows bacterial counts in tortilla prepared from nixtamalized corn flour without additive (control), with commercial organic acid or with Maseca-1 extract. Either water (control), organic acid or extract was added to the flour or dough and tortillas were prepared soon thereafter—about 0.5-1 hours after the dough was prepared. The tortillas were then stored at 25° C. for three (3) days. In Test 1, the bacteria counts (CFU/g) were lower in the tortilla prepared with the added Maseca-1 extract ($1.4 \times 10^6$) compared to control ($7.5 \times 10^6$), but higher than that of the organic acid ($0.15 \times 10^6$). In Test 2, the bacteria counts were again lower in the tortilla prepared with the added Maseca-1 extract ($17.9 \times 10^6$) compared to control ($27.0 \times 10^6$), but higher than that of the organic acid ($7.56 \times 10^6$).

Lime-heat treatment in corn flour and heat-cooking in dough for tortilla making did not eliminate thermoduric/thermophilic bacteria or sporeformer microflora even though their bacteria counts were acceptable (<1000 CFU/g). Organoleptic changes occurred in the control tortilla (without additive) with a pungent acid aroma after 3 days shelf life at 25° C. Bacteria (*Lactobacillus* sp., *Streptococcus* sp., *Bacillus* sp.) have been found in the natural or acidic fermentation of corn meal (Fields et al., J. Food Sci. (1981) 46:900).

Figure 9A:
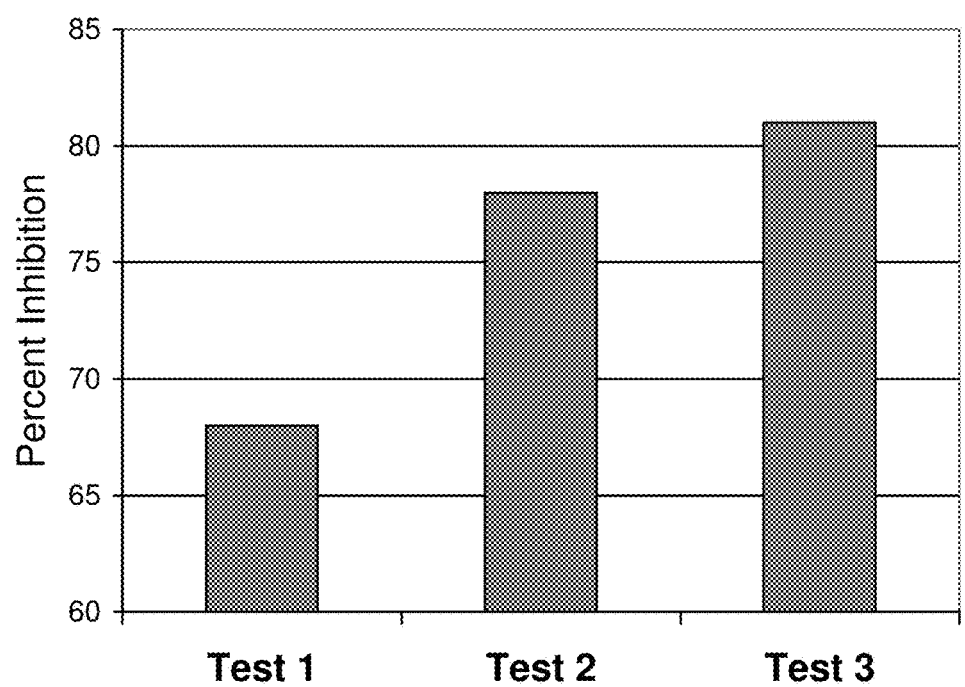
FIGS. 9A, 9B and 9C are microbial inhibition graphs illustrating the reduction (percentage) in bacteria (9A) and molds (9B) in corn dough with the Maseca-1 extract, and reduction in bacteria in tortilla (9C) with the Maseca-1 extract or organic acid additive after 3 days storage at 25° C.
Figure 9B:
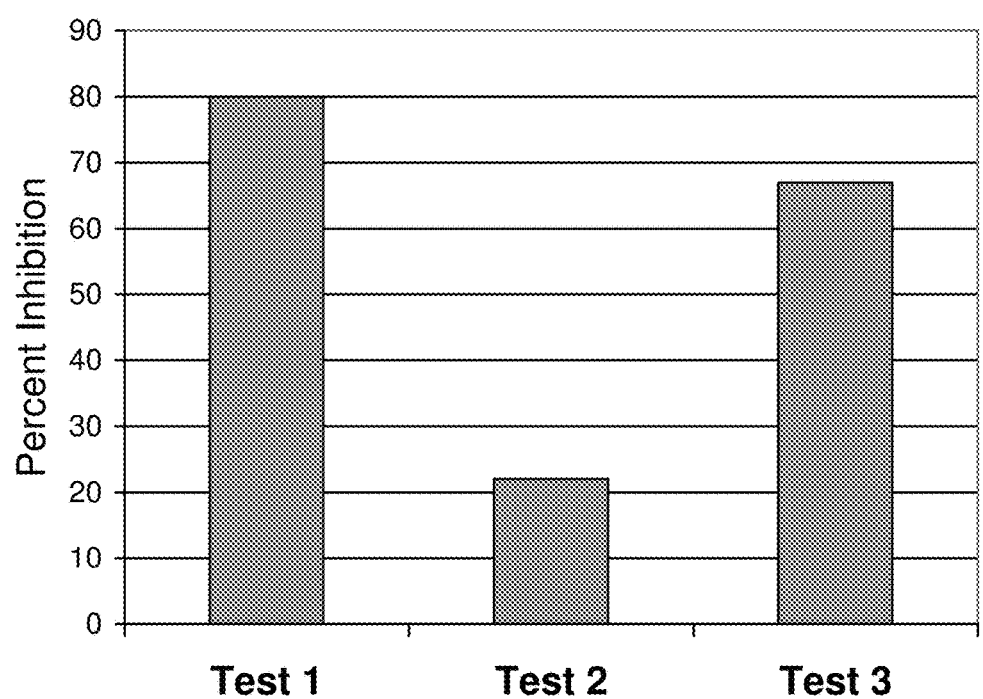

FIG. 9A and 9B illustrate the inhibition of bacteria and mold growth in corn dough resulting from the addition of the Maseca-1 extract. The extract was added to the corn flour and dough was prepared. The dough was analyzed for bacteria and mold about 0.5-1.0 hour after the dough was prepared. In three separate experiments, the inhibition of bacterial growth ranged from 68% to 81% (FIG. 9A) and the inhibition of mold growth ranged from 22% to 80% (FIG. 9B).

Figure 9C:
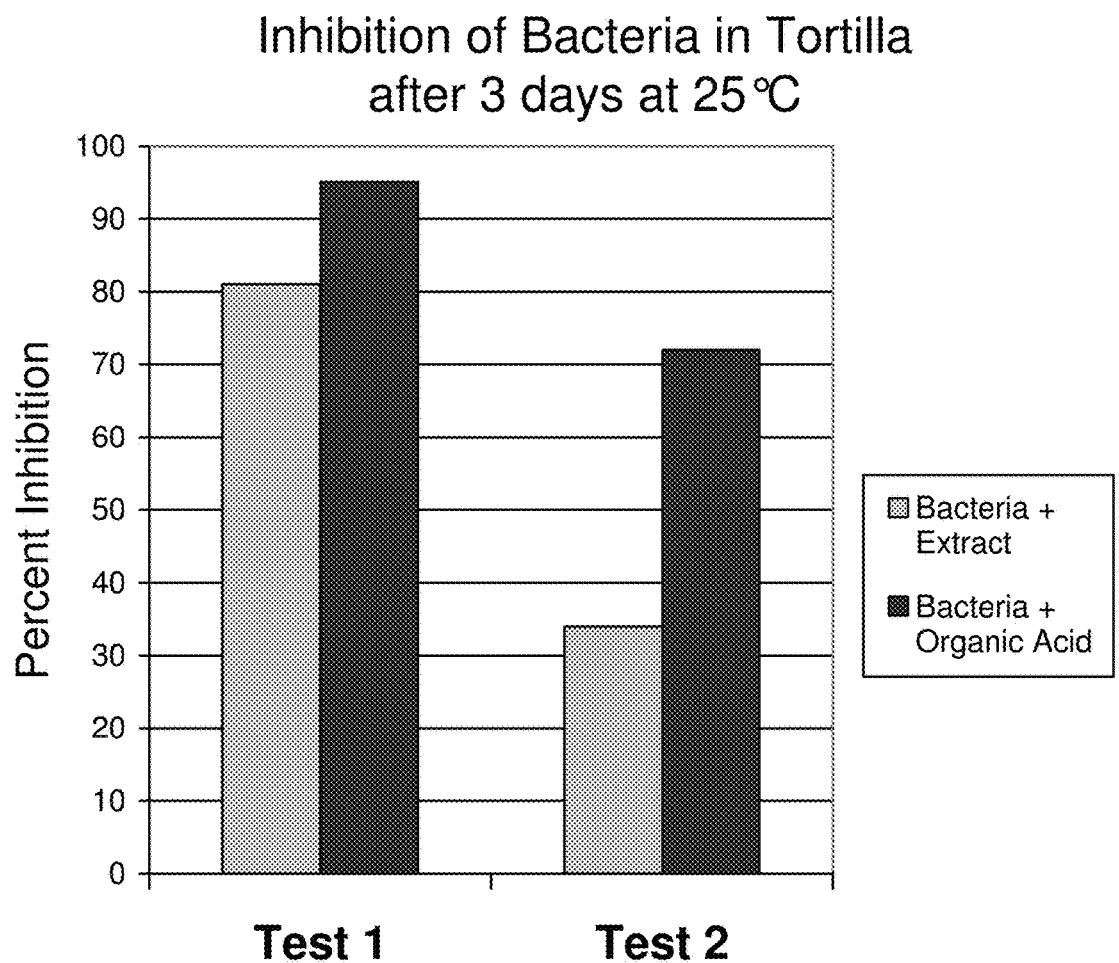

In FIG. 9C, the bacteria inhibition in the Maseca-1 extract is compared to that of the commercial organic acid material. The bacteria were counted in tortilla after 3 days storage at 25° C. In two separate experiments, the tortilla with the Maseca-1 extract showed a lower but comparable amount of bacterial inhibition (inactivation or bacteriostatic effect) compared to the organic acid additive, but still an effective amount of inhibition.

Due to the addition of the Maseca-1 extract during hydration of nixtamalized corn flour and dough kneading, the bacteria count in the dough (0 days) was decreased about 75%, and the mold count was decreased about 55%. A bacterial count reduction of about 60% was found in the Maseca-1 extract tortilla after three days storage at 25° C.

According to various embodiments of the invention, biologically pure cultures of *Bacillus subtilis* are provided. The Maseca-1 strain of *Bacillus subtilis* has been deposited under ATCC accession number PTA-8831.

The *Bacillus subtilis* Maseca-1 cultures are capable of producing secreted proteins and/or peptide antibiotics that have antimicrobial activity (e.g., lantibiotics). These secreted linear or globular structure peptides and proteins are useful in compositions according to the present invention. Cell cultures from Maseca-1 can be harvested and the culture supernatants collected, for example, by filtration (filtered supernatant), differential precipitation, or centrifugation (cell free supernatant) and the resulting supernatant can contain antimicrobial activities useful in an antimicrobial composition.

The Maseca-1 strain can secrete one or more proteins or peptides that inhibit the growth of microorganisms, including Gram-positive and Gram-negative bacteria, molds and yeasts. For example, the secreted protein or peptide can inhibit the growth of Gram-positive pathogens *Micrococcus luteus* and *Bacillus cereus* and of *Aspergillus flavus*.

The *Bacillus subtilis* Maseca-1 may be active against Gram-negative and Gram-positive bacteria, as well as molds and yeasts, which are common spoilage flora in foods. Many Gram-negative bacteria such as *Salmonella*, *Shigella*, certain serological types of *Escherichia*, and the like are food-borne pathogens. Gram-positive bacteria, such as *Bacillus cereus, Staphylococcus aureus, Clostridium perfringens* and the like can cause food poisoning.

According to embodiments of the present invention, the *Bacillus subtilis* Maseca-1 produces compounds that inhibit the growth of microorganisms, such as bacteria and molds. The compounds can be secreted proteins or peptides. According to one embodiment, the compounds that inhibit the growth of the microorganisms are contained in an extract of the cultured Maseca-1 in which a filtrate of <10KDa is prepared (Maseca-1 extract).

The Maseca-1 extract can be added to food, food materials or food products and an effective amount of the extract can inhibit the growth of undesired microorganisms. The Maseca-1 extract can reduce or prevent spoilage of food and food products and thereby extend their shelf-life.

The Maseca-1 extract can be added to corn and wheat dough and used to control mold and bacterial growth, for example, in tortillas and flat breads. Similar preparations can be used for various breads, flat breads, baked goods and the like, where dough is the starting material. The Maseca-1 extract can be used for inhibiting molds and bacteria, extending shelf-life, and preserving dough during handling or transportation to a baking site. The Maseca-1 extract can also be used to suppress molds and bacteria and extend shelf-life in dairy products such as milk, cream, dairy spreads and cheese.

An effective amount of the Maseca-1 extract can be determined by those in the art. An amount of extract that can effectively inhibit the growth of undesirable microorganisms can be about 0.001 g to 10 g of extract per 100 g of food, food materials or food product, for example, about 0.01 g or about 0.1 g to about 1.0 g.

According to various embodiments, the present invention also relates to a method for inhibiting undesirable microorganisms in a material containing or exposed to the microorganisms. The method includes exposing the material to an inhibitor of the undesired microorganisms obtained from *Bacillus subtilis* Maseca-1 so that the undesired microorganisms in the material are inhibited. The material to be protected can be, for example, a material in contact with a food. The food can be for any animal, particularly mammals.

The *Bacillus subtilis* Maseca-1 can be living or non-living. If living, Maseca-1 can be frozen or lyophilized or otherwise dried for preservation. The growth inhibition of microorganisms can be produced by a component of Maseca-1 and thus Maseca-1 can be non-living. It can be sonicated or otherwise disrupted for cell wall fraction recovery and preservation prior to use. All of these variations are known to those skilled in the art.

According to various embodiments of the invention, the *Bacillus subtilis* Maseca-1 can be used to control mold growth in grains, for example in stored grain, and in legumes, and in underground crops like peanuts. Such a treatment can be used to prevent mycotoxin formation (e.g., aflatoxins and fumonisins) in various cereal grains, legumes and peanuts.

One of the major problems in the distribution and marketing of tortillas is the appearance of mold spots and patches of mold discoloration on packaged tortillas. According to various embodiments, the *Bacillus subtilis* Maseca-1 bacteria can be added to the corn and wheat dough and used to control mold and bacterial growth, for example, in tortillas and flat breads. Similar preparations can be used for various breads, flat breads, baked goods and the like, where dough is the starting material. The *Bacillus subtilis* Maseca-1 bacteria can be used for inhibiting molds and bacteria, extending shelf-life, and preserving dough during handling or transportation to a baking site. Maseca-1 can also be used to suppress molds and bacteria and extend shelf-life in dairy products such as milk, cream, dairy spreads and cheese.

*Bacillus subtilis* Maseca-1 can be applied to packaging materials to suppress microflora of foods. Maseca-1 can thus be used to treat films, casings and other packaging materials to control mold and bacterial growth on various food products like breads, cheeses, sausages, vegetables, fruits and the like.

According to various embodiments of the invention, *Bacillus subtilis* Maseca-1 can produce natural biopolymers such as high molecular weight and branched fructan made up of fructose units linked by β-(2,6) fructofuranoside bonds and inulin β-(2,1) linkages.

According to various embodiments, the *Bacillus subtilis* Maseca-1 can produce the enzyme levan sucrase, for example, β-(2,6) fructan-D:glucose-1-fructosyltransferase (E.C.2.4.1.10).

The present invention also contemplates the use of *Bacillus subtilis* Maseca-1 as a probiotic for biologically controlling various microbial infections in the intestinal tract. Because *B. subtilis* forms heat-resistant spores, this species is particularly useful for making pharmaceutical compositions for treating microbial infections. Formulations that include viable Maseca-1 spores in a pharmaceutically acceptable carrier can be utilized for making and using both prophylactic and therapeutic compositions.

According to various embodiments, a probiotic composition contains viable *Bacillus subtilis* Maseca-1. The composition can also include a carrier such as a pharmaceutically acceptable carrier suitable for oral administration to the digestive tract of a subject. The composition can include Maseca-1 in the form of vegetative cells and/or spores. In another embodiment, the invention provides for including Maseca-1 in a composition in the form of a dried cell mass, a stabilized paste, or a stabilized gel.

Because *Bacillus* spores are heat and pressure-resistant and can be stored as a dry powder, they are particularly useful in the formulation and manufacture of products such as various baked products (e.g., tortillas and flat breads and the like). *Bacillus subtilis* Maseca-1 is well suited for the present invention, having the ability to form spores which are relatively resistant to heat and other conditions, making them ideal for improving storage (i.e., shelf-life) of food products. For example, *Bacillus subtilis* Maseca-1 can survive storage for two or more years.

According to various embodiments, *Bacillus subtilis* Maseca-1 is present in the probiotic composition or baked product at a concentration of $10^3$-$10^{12}$ viable cells/g, for example concentrations of $10^5$-$10^7$ viable cells/g, $10^8$-$10^9$ viable cells/g or $10^9$-$10^{10}$ viable cells/g.

In some embodiments, the probiotic composition also contains at least one digestive enzyme, for example, amylase, pullulanase, protease, phytase, xylanase, glucanase, levanase or galactosidase.

In some embodiments of the probiotic composition, the vegetative cells and/or spores can be encapsulated or coated into a biodegradable or bioresorbable polymer in order to protect them against digestive enzymes and conditions in the digestive tract.

In another embodiment, there is provided a composition that includes an extracellular product of *Bacillus subtilis* Maseca-1 in a pharmaceutically acceptable carrier suitable for oral administration to a human. In one embodiment, the extracellular product is a supernatant or filtrate of a culture of Maseca-1. The extracellular product can be, for example, levans, enzymes and/or lantibiotics.

The present invention contemplates a method for treating, reducing or controlling bacterial gastrointestinal infections using a prophylactic and/or therapeutic composition or system that includes the *Bacillus subtilis* Maseca-1. These methods can inhibit pathogenic bacterial growth associated with gastrointestinal infections and also reduce symptoms of these pathogenic infections. Because *Bacillus subtilis* are generally regarded as safe by those skilled in the art, they are very suitable for ingestion in food stuffs or as a food supplement.

Another embodiment of the invention provides a method of modulating digestion in a human or an animal by orally administering to the human or animal a probiotic food composition having *Bacillus subtilis* Maseca-1 in a quantity sufficient to obtain a desired level of modulation. The modulation can, for example, improve the intake of nutrients, reduce pathogens or improve the growth of beneficial commensal microorganisms.

According to various embodiments, a method of preventing or treating a bacterial gastrointestinal infection in a human or animal comprises the steps of orally administering to a human or animal subject a food or drink formulation containing viable colony forming units of *Bacillus subtilis* Maseca-1, and allowing the bacteria to grow in the subject's gastrointestinal tract. In one embodiment, the viable colony forming units are spores of Maseca-1. The Maseca-1 can reduce disorders caused by infectious agents, such as *Staphylococcus aureus, S. epidermidis, Streptococcus pyogenes, Escherichia coli, Pseudomonas aeruginosa, Listeria monocytogenes, Clostridium* species including *C. perfingens, C. difficile, C. botulinum, C. tributrycum*, and *C. sporogenes*, pathogenic-*B. cereus, Gardnerella vaginalis, Propionibacterium acnes, Aeromonas hydrophilia, Aspergillus* sp. including *A. flavus* and *A. niger, Proteus, Klebsiella, Salmonella, Shigella, Yersinia* and *Campylobacter.*

The probiotic effects of *Bacillus subtilis* Maseca-1 can occur because the microorganism colonizes the mucosa of the gut wall and out-competes potential pathogens. The probiotic *Bacillus subtilis* Maseca-1 can also produce i) organic and carboxylic acids such as short-chain fatty acids which show antimicrobial activity towards many microorganisms, and decrease the pH and the redox potential in the gut, creating suboptimal conditions for pathogens, ii) metabolites such as proteins (i.e., enzymes) and exopolysaccharides (i.e., levans and glucans) which are antagonistic to some pathogens through inhibition of their ability to take up nutrients and ions or their adhesion to intestinal mucosa cells, and iii) bacteriocins and bacteriocin-like products (i.e., lantibiotics) which exert their effects by disruption of energy production systems, macromolecule synthesis and membrane permeability.

It will be recognized by one of ordinary skill in the art that the probiotic *Bacillus subtilis* Maseca-1 can be found in the form of spores, or accompanied by microbial spores. In general, bacterial spores are thick-walled, dormant forms which are capable of surviving unfavorable conditions. These dietary adjuncts or direct-fed microbials can complete their entire life cycle within the gastrointestinal tract, going from spore to vegetative cell and sporulating again.

Another embodiment of the invention provides a new formulation of animal food supplement or live microbial supplement based on synergistic and/or additional beneficial effects such as probiotic, prebiotic and other ingredients such as enzymes, vitamins and minerals. The formulation can be, for example, a nutritional supplement in powdered form containing a probiotic system of *Bacillus subtilis* Maseca-1, prebiotic components (e.g., nondigestible oligomers of fructose, glucose and galactose or sugar acids and alcohols) and enzymes. The powdered nutritional supplement can contain from about $10^3$-$10^{12}$ viable organisms/gram, for example, about $10^8$ viable organisms/gram.

The present invention also includes methods of improving intestinal digestibility, growth rate, and feed conversion of various animal species by incorporating the above food supplement in the animal diet. Animal species include but are not limited to cows, pigs, chickens and turkeys. The host animal's intestinal microbiota can be modulated by both introducing the *Bacillus subtilis* Maseca-1 and/or by stimulating endogenous Maseca-1 with prebiotics.

According to another embodiment, the present invention relates to a synbiotic composition that includes viable *Bacillus subtilis* Maseca-1. The synbiotic composition can be used, for example, in combination with bifidogenic and lactobacillogenic oligosaccharides that are particularly useful for preferentially promoting the growth of *Bacillus subtilis* Maseca-1. These oligosaccharides include fructooligosaccharides (FOS) from branched levan and linear inulin, galactooligosaccharides (GOS), xylooligosaccharides (XOS), sugar acids (glucuronic and galacturonic acid), sugar alcohols (lactitol and xylitol) and other long-chain polymers (lignin and glycoproteins) that are not readily digested by pathogenic bacteria. The preferential growth is promoted due to the nutrient requirements of *Bacillus subtilis* Maseca-1 as compared to pathogenic bacteria. Deleterious bacteria such as *Clostridium, Staphylococcus, Salmonella* and *E. coli* cannot metabolize FOS, GOS, XOS, or other bifidogenic and lactobacillogenic oligosaccharides and therefore use of these oligosaccharides in combination with *Bacillus subtilis* Maseca-1 allows these beneficial and probiotic bacteria to grow and to replace the undesirable or pathogenic microorganisms.

The bifidogenic and lactobacillogenic oligosaccharides can be used either alone or in combination with *Bacillus subtilis* Maseca-1 in a synbiotic or prophylactic and therapeutic composition. That is, due to the growth promoting activity of bifidogenic and lactobacillogenic oligosaccharides, the invention contemplates a composition comprising a bifidogenic and lactobacillogenic oligosaccharide in a *Bacillus* growth-promoting amount. These amounts can vary widely since the probiotic will respond to any metabolic amount of nutrient oligosaccharide, and therefore the invention need not be so limited.

What is claimed is:

1. A method of inhibiting the growth of microorganisms in a food, food material or food product, comprising adding an effective amount of a cell-free extract prepared from *Bacillus subtilis* to said food, food material or food product, wherein the *Bacillus subtilis* is the Maseca-1 strain, deposited under ATCC accession number PTA-8831, and wherein the effective amount of the extract is in a range of from 0.1 g to 1 g of extract per 100 g of food, food material or food product.

2. The method of claim 1, wherein the extract comprises a filtrate of <10 kDa.

3. The method of claim 1, wherein the food, food material or food product is flour, dough or a cooked dough product.

4. The method of claim 1, wherein the food, food material or food product is corn flour, corn dough or tortilla.

5. The method of claim 1, wherein the growth of said microorganisms is inhibited for at least 3 days.

6. The method of claim 1, wherein the microorganisms are bacteria and mold.

7. A method of extending the shelf life of a food, food material or food product, comprising adding an effective amount of an extract prepared from *Bacillus subtilis* to said food, food material or food product, wherein the *Bacillus subtilis* is the Maseca-1 strain, deposited under ATCC accession number PTA-8831.

8. The method of claim 1, wherein the cell-free extract comprises amphiphilic compounds produced in supernatant of cultured said *Bacillus subtilis* Maseca-1 strain.

* * * * *